(12) United States Patent
Johnston et al.

(10) Patent No.: US 8,728,179 B2
(45) Date of Patent: *May 20, 2014

(54) ETHANOL COMPOSITIONS

(75) Inventors: Victor Johnston, Houston, TX (US);
Lincoln Sarager, Houston, TX (US); R. Jay Warner, Houston, TX (US); Heiko Weiner, Pasadena, TX (US); Trinity Horton, Houston, TX (US); Radmila Jevtic, Pasadena, TX (US)

(73) Assignee: Celanese International Corporation, Dallas, TX (US)

( * ) Notice: Subject to any disclaimer, the term of this patent is extended or adjusted under 35 U.S.C. 154(b) by 344 days.

This patent is subject to a terminal disclaimer.

(21) Appl. No.: 13/197,743

(22) Filed: Aug. 3, 2011

(65) Prior Publication Data

US 2012/0041075 A1     Feb. 16, 2012

Related U.S. Application Data

(63) Continuation-in-part of application No. 12/852,290, filed on Aug. 6, 2010, now Pat. No. 8,460,405, and a continuation-in-part of application No. 12/889,260, filed on Sep. 23, 2010.

(60) Provisional application No. 61/300,815, filed on Feb. 2, 2010, provisional application No. 61/332,727, filed on May 7, 2010, provisional application No. 61/332,696, filed on May 7, 2010, provisional application No. 61/332,699, filed on May 7, 2010, provisional application No. 61/332,728, filed on May 7, 2010, provisional application No. 61/346,344, filed on May 19, 2010.

(51) Int. Cl.
*C10L 1/18* (2006.01)

(52) U.S. Cl.
USPC ............................................. 44/452; 44/451

(58) Field of Classification Search
USPC .................................................. 44/451, 452
See application file for complete search history.

(56) References Cited

U.S. PATENT DOCUMENTS

| | | |
|---|---|---|
| 1,939,116 A | 12/1933 | Fuchs |
| 2,105,540 A | 1/1938 | Lazier |
| 2,192,137 A | 2/1940 | Kvalnes |
| 2,549,416 A | 4/1951 | Brooks |
| 2,607,807 A | 8/1952 | Ford |
| 2,649,407 A | 8/1953 | Harrison et al. |
| 2,702,783 A | 2/1955 | Harrison et al. |

(Continued)

FOREIGN PATENT DOCUMENTS

| | | |
|---|---|---|
| CN | 1230458 | 10/1999 |
| CN | 102091429 | 6/2011 |

(Continued)

OTHER PUBLICATIONS

International Search Report and Written Opinion mailed Apr. 23, 2012 in corresponding International Application No. PCT/US2011/046493.

(Continued)

*Primary Examiner* — Cephia D Toomer

(57) ABSTRACT

In one embodiment, the present invention is to an ethanol composition comprising at least 85 wt. % ethanol and from 95 wppm to 850 wppm isopropanol.

90 Claims, 3 Drawing Sheets

(56) References Cited

U.S. PATENT DOCUMENTS

| | | |
|---|---|---|
| 2,744,939 A | 5/1956 | Kennel |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,702,886 A | 11/1972 | Argauer et al. |
| 3,729,429 A | 4/1973 | Robson |
| 3,769,329 A | 10/1973 | Knox et al. |
| 3,847,756 A | 11/1974 | Statman et al. |
| 3,953,524 A | 4/1976 | Steiner |
| 3,990,952 A | 11/1976 | Katzen et al. |
| 4,052,467 A | 10/1977 | Mills et al. |
| 4,065,512 A | 12/1977 | Cares |
| 4,270,015 A | 5/1981 | Knifton et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,328,373 A | 5/1982 | Strojny |
| 4,337,351 A | 6/1982 | Larkins |
| 4,379,028 A | 4/1983 | Berg et al. |
| 4,395,576 A | 7/1983 | Kwantes et al. |
| 4,398,039 A | 8/1983 | Pesa et al. |
| 4,399,305 A | 8/1983 | Schreck et al. |
| 4,421,939 A | 12/1983 | Kiff et al. |
| 4,422,903 A | 12/1983 | Messick et al. |
| 4,426,541 A | 1/1984 | King |
| 4,443,639 A | 4/1984 | Pesa et al. |
| 4,451,677 A | 5/1984 | Bradley et al. |
| 4,454,358 A | 6/1984 | Kummer et al. |
| 4,465,854 A | 8/1984 | Pond et al. |
| 4,465,875 A | 8/1984 | Greenbank et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,514,515 A | 4/1985 | Travers et al. |
| 4,517,391 A | 5/1985 | Schuster et al. |
| 4,520,213 A | 5/1985 | Victor |
| 4,521,630 A | 6/1985 | Wattimena et al. |
| 4,527,995 A | 7/1985 | Itow et al. |
| 4,541,897 A | 9/1985 | Sommer et al. |
| 4,550,185 A | 10/1985 | Mabry et al. |
| 4,559,109 A | 12/1985 | Lee et al. |
| 4,569,726 A | 2/1986 | Berg et al. |
| 4,581,473 A | 4/1986 | Polichnowski |
| 4,592,806 A | 6/1986 | Ilgner et al. |
| 4,613,700 A | 9/1986 | Maki et al. |
| 4,626,321 A | 12/1986 | Grethlein et al. |
| 4,626,604 A | 12/1986 | Hiles et al. |
| 4,678,543 A | 7/1987 | Houben et al. |
| 4,692,218 A | 9/1987 | Houben et al. |
| 4,696,596 A | 9/1987 | Russell et al. |
| 4,760,171 A | 7/1988 | Isogai et al. |
| 4,762,817 A | 8/1988 | Logsdon et al. |
| 4,777,303 A | 10/1988 | Kitson et al. |
| 4,804,791 A | 2/1989 | Kitson et al. |
| 4,826,795 A | 5/1989 | Kitson et al. |
| 4,842,693 A | 6/1989 | Wheldon |
| 4,876,402 A | 10/1989 | Logsdon et al. |
| 4,886,905 A | 12/1989 | Larkins et al. |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,004,845 A | 4/1991 | Bradley et al. |
| 5,008,235 A | 4/1991 | Wegman et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg et al. |
| 5,093,534 A | 3/1992 | Ludwig et al. |
| 5,124,004 A | 6/1992 | Grethlein et al. |
| 5,137,861 A | 8/1992 | Shih et al. |
| 5,144,068 A | 9/1992 | Smith et al. |
| 5,149,680 A | 9/1992 | Kitson et al. |
| 5,155,084 A | 10/1992 | Horn et al. |
| 5,185,308 A | 2/1993 | Bartley et al. |
| 5,185,481 A | 2/1993 | Muto et al. |
| 5,206,434 A | 4/1993 | Scates et al. |
| 5,215,902 A | 6/1993 | Tedder |
| 5,233,099 A | 8/1993 | Tabata et al. |
| 5,237,108 A | 8/1993 | Marraccini et al. |
| 5,241,106 A | 8/1993 | Inoue et al. |
| 5,243,095 A | 9/1993 | Roberts et al. |
| 5,250,271 A | 10/1993 | Horizoe et al. |
| 5,284,983 A | 2/1994 | Muto et al. |
| 5,306,845 A | 4/1994 | Yokohama et al. |
| 5,334,769 A | 8/1994 | Ferrero et al. |
| 5,348,625 A | 9/1994 | Berg |
| 5,350,504 A | 9/1994 | Dessau |
| 5,399,752 A | 3/1995 | Okrasinski et al. |
| 5,415,741 A | 5/1995 | Berg |
| 5,426,246 A | 6/1995 | Nagahara et al. |
| 5,437,770 A * | 8/1995 | Berg ............................. 203/57 |
| 5,445,716 A | 8/1995 | Berg |
| 5,449,440 A | 9/1995 | Rescalli et al. |
| 5,475,144 A | 12/1995 | Watson et al. |
| 5,476,827 A | 12/1995 | Ferrero et al. |
| 5,480,665 A | 1/1996 | Smith |
| 5,488,185 A | 1/1996 | Ramachandran et al. |
| 5,502,248 A | 3/1996 | Funk et al. |
| 5,527,969 A | 6/1996 | Kaufhold et al. |
| 5,565,068 A | 10/1996 | Parker et al. |
| RE35,377 E | 11/1996 | Steinberg et al. |
| 5,585,523 A | 12/1996 | Weiguny et al. |
| 5,599,976 A | 2/1997 | Scates et al. |
| 5,663,430 A | 9/1997 | Morris et al. |
| 5,720,784 A | 2/1998 | Killick et al. |
| 5,762,765 A | 6/1998 | Berg |
| 5,767,307 A | 6/1998 | Ramprasad et al. |
| 5,770,770 A | 6/1998 | Kim et al. |
| 5,800,681 A | 9/1998 | Berg |
| 5,821,111 A | 10/1998 | Grady et al. |
| 5,849,657 A | 12/1998 | Rotgerink et al. |
| 5,858,031 A | 1/1999 | Perlman |
| 5,861,530 A | 1/1999 | Atkins et al. |
| 5,945,570 A | 8/1999 | Arhancet et al. |
| 5,955,397 A | 9/1999 | Didillon et al. |
| 5,973,193 A | 10/1999 | Crane et al. |
| 5,993,610 A | 11/1999 | Berg |
| 6,040,474 A | 3/2000 | Jobson et al. |
| 6,049,008 A | 4/2000 | Roberts et al. |
| 6,093,845 A | 7/2000 | Van Acker et al. |
| 6,114,571 A | 9/2000 | Abel et al. |
| 6,121,498 A | 9/2000 | Tustin et al. |
| 6,140,535 A | 10/2000 | Williams |
| 6,143,930 A | 11/2000 | Singh et al. |
| 6,232,352 B1 | 5/2001 | Vidalin et al. |
| 6,232,504 B1 | 5/2001 | Barteau et al. |
| 6,294,703 B1 | 9/2001 | Hara et al. |
| 6,375,807 B1 | 4/2002 | Nieuwoudt et al. |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,559,333 B1 | 5/2003 | Brunelle et al. |
| 6,603,038 B1 | 8/2003 | Hagemeyer et al. |
| 6,627,770 B1 | 9/2003 | Cheung et al. |
| 6,632,330 B1 | 10/2003 | Cooley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,723,886 B2 | 4/2004 | Allison et al. |
| 6,727,380 B2 | 4/2004 | Ellis et al. |
| 6,765,110 B2 | 7/2004 | Warner et al. |
| 6,768,021 B2 | 7/2004 | Horan et al. |

(56) References Cited

U.S. PATENT DOCUMENTS

| | | | |
|---|---|---|---|
| 6,809,217 B1 | 10/2004 | Colley et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,297,236 B1 | 11/2007 | Vander Griend et al. |
| 7,351,559 B2 | 4/2008 | Verser et al. |
| 7,375,049 B2 | 5/2008 | Hayes et al. |
| 7,399,892 B2 | 7/2008 | Rix et al. |
| 7,425,657 B1 | 9/2008 | Elliott et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,572,353 B1 | 8/2009 | Vander Griend |
| 7,601,865 B2 | 10/2009 | Verser et al. |
| 7,608,744 B1 | 10/2009 | Johnston et al. |
| 7,678,940 B2 | 3/2010 | Miura et al. |
| 7,682,812 B2 | 3/2010 | Verser et al. |
| 7,700,814 B2 | 4/2010 | Garton et al. |
| 7,718,039 B2 | 5/2010 | Dirkzwager et al. |
| 7,732,173 B2 | 6/2010 | Mairal et al. |
| 7,744,727 B2 | 6/2010 | Blum et al. |
| 7,816,565 B2 | 10/2010 | Johnston et al. |
| 7,820,852 B2 | 10/2010 | Johnston et al. |
| 7,834,223 B2 | 11/2010 | Atkins et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,947,746 B2 | 5/2011 | Daniel et al. |
| 8,071,821 B2 | 12/2011 | Johnston et al. |
| 2003/0004057 A1 | 1/2003 | Yamaguchi et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bharadwaj et al. |
| 2004/0195084 A1 | 10/2004 | Hetherington et al. |
| 2005/0028435 A1 | 2/2005 | Pace et al. |
| 2005/0176996 A1 | 8/2005 | Law et al. |
| 2006/0019360 A1 | 1/2006 | Verser et al. |
| 2006/0102520 A1 | 5/2006 | Lapinsky et al. |
| 2006/0106246 A1 | 5/2006 | Warner et al. |
| 2006/0127999 A1 | 6/2006 | Verser et al. |
| 2007/0031954 A1 | 2/2007 | Mairal et al. |
| 2007/0238906 A1 | 10/2007 | Brown et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0209786 A1 | 8/2009 | Scates et al. |
| 2009/0221725 A1 | 9/2009 | Chorney et al. |
| 2009/0274480 A1 | 11/2009 | Zona |
| 2009/0281354 A1 | 11/2009 | Mariansky et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029993 A1 | 2/2010 | Johnston et al. |
| 2010/0029995 A1 | 2/2010 | Johnston et al. |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0069514 A1 | 3/2010 | Gracey et al. |
| 2010/0069515 A1 | 3/2010 | Tirtowidjojo et al. |
| 2010/0113843 A1 | 5/2010 | Lee et al. |
| 2010/0121114 A1 | 5/2010 | Johnston et al. |
| 2010/0125148 A1 | 5/2010 | Johnston et al. |
| 2010/0137630 A1 | 6/2010 | Garton et al. |
| 2010/0168467 A1 | 7/2010 | Johnston et al. |
| 2010/0168493 A1 | 7/2010 | Le Peltier et al. |
| 2010/0185021 A1 | 7/2010 | Ross et al. |
| 2010/0196789 A1 | 8/2010 | Fisher et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0249479 A1 | 9/2010 | Berg-Slot et al. |
| 2011/0004033 A1 | 1/2011 | Johnston et al. |
| 2011/0046421 A1 | 2/2011 | Daniel et al. |
| 2011/0071312 A1 | 3/2011 | Johnston et al. |
| 2011/0082322 A1 | 4/2011 | Jevtic et al. |
| 2011/0098513 A1 | 4/2011 | Weiner et al. |
| 2011/0190547 A1 | 8/2011 | Jevtic et al. |
| 2011/0190548 A1 | 8/2011 | Jevtic et al. |
| 2011/0275862 A1 | 11/2011 | Johnston et al. |

FOREIGN PATENT DOCUMENTS

| | | |
|---|---|---|
| CN | 102228831 | 11/2011 |
| CN | 102229520 | 11/2011 |
| DE | 27 23 611 A1 | 11/1978 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0330853 | 9/1989 |
| EP | 0372847 | 6/1990 |
| EP | 0400904 | 12/1990 |
| EP | 0408528 | 1/1991 |
| EP | 0456647 | 11/1991 |
| EP | 0539274 | 4/1993 |
| EP | 0557786 | 9/1993 |
| EP | 0990638 | 10/1998 |
| EP | 0953560 | 11/1999 |
| EP | 0992482 | 4/2000 |
| EP | 0992484 | 4/2000 |
| EP | 1262234 | 12/2002 |
| EP | 1277826 | 1/2003 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 745946 | 3/1956 |
| GB | 1168785 | 10/1969 |
| GB | 1559540 | 1/1980 |
| GB | 2136704 | 9/1984 |
| JP | 4193304 | 7/1992 |
| JP | 6-116182 | 4/1994 |
| JP | 10-306047 | 11/1998 |
| JP | 11-147845 | 6/1999 |
| JP | 2000-178487 | 6/2000 |
| JP | 2001-046874 | 2/2001 |
| JP | 2001-157841 | 6/2001 |
| JP | 2010-159212 A | 7/2010 |
| WO | WO 83/03409 | 10/1983 |
| WO | WO 03/040037 | 5/2003 |
| WO | WO 03/106396 | 12/2003 |
| WO | WO 2007/003897 | 1/2007 |
| WO | WO 2007/145490 A1 | 12/2007 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |

(56) References Cited

FOREIGN PATENT DOCUMENTS

| | | |
|---|---|---|
| WO | WO 2009/105860 | 9/2009 |
| WO | WO 2010/014145 | 2/2010 |
| WO | WO 2010/014146 | 2/2010 |
| WO | WO 2010/014148 | 2/2010 |
| WO | WO 2010/014151 | 2/2010 |
| WO | WO 2010/014152 | 2/2010 |
| WO | WO 2010/014153 | 2/2010 |
| WO | WO 2010/055285 | 5/2010 |
| WO | WO 2010/056299 | 5/2010 |
| WO | WO 2011/053365 | 5/2011 |
| WO | WO 2011/097194 | 8/2011 |

OTHER PUBLICATIONS

International Preliminary Report on Patentability mailed Jun. 27, 2012 in corresponding International Application No. PCT/US2011/023322.
Written Opinion mailed May 8, 2012 in corresponding International Application No. PCT/US2011/023322.
International Search Report and Written Opinion mailed Sep. 6, 2011 in corresponding International Application No. PCT/US2011/023322.
International Search Report and Written Opinion mailed Jun. 7, 2010 in corresponding International Application No. PCT/US2010/022947.
International Search Report and Written Opinion mailed May 21, 2012 in corresponding International Application No. PCT/US2011/046502.
International Search Report mailed Feb. 2, 2012 in corresponding International Application No. PCT/US2011/046500.
International Search Report and Written Opinion mailed Jul. 18, 2011 in corresponding International Application No. PCT/US2011/023278.
International Preliminary Report on Patentability mailed May 18, 2012 in corresponding International Application No. PCT/US2011/023278.
Invitation to Pay Fees mailed Jul. 24, 2012 in corresponding International Application No. PCT/US2011/046511.
U.S. Office Action mailed Jun. 20, 2012 in corresponding U.S. Appl. No. 13/273,054.
Zhang et al., Hydrogenation of Ethyl Acetate to Ethanol over Ni-Based Catalysts Obtained from Ni/Al Hydrotalcite-Like Compounds. Molecules 2010, 15, 5139-5152, 2010.
Pestman et al., The formation of ketones and aldehydes from carboxylic acids, structure-activity relationship for two competitive reactions, Journal of Molecular Catalysis A: Chemical 103 Jun. 14, 1995, 175-180.
Waterland, et al., "Safety and Performance Assessment of Ethanol/Diesel Blends (e-blend)", NREL/SR-540-34817, at p. 1-1, Sep. 2003.
J. Jones, et al., Platinum Metals Review, vol. 44, No. 3, pp. 94-104 (Jul. 2000).
Proc. Roy Soc. A314, pp. 473-498 (1970).
International Fuel Quality Center Hart Downstream Energy Services: "Setting a quality standard for fuel ethanol—DEH ethanol standard 18/2004 report", Jan. 1, 2004, pp. 1-56.
Ivan Hodac, et al., "Ethanol Guidelines", Mar. 1, 2009, pp. 1-12.
International Search Report and Written Opinion for PCT/US2010/054136 mailed May 25, 2010.
International Search Report and Written Opinion for PCT/US2011/023338 mailed Sep. 6, 2011.
International Search Report for PCT/US2011/023269 mailed Aug. 25, 2010.
International Search Report for PCT/US2011/046508 dated Mar. 29, 2012.
International Search Report for PCT/US2011/046500 dated Mar. 29, 2012.
International Search Report and Written Opinion for PCT/US2009/004197 mailed Mar. 24, 2010 (14 pages).
International Search Report and Written Opinion for PCT/US2009/004195 mailed Mar. 26, 2010 (12 pages).
International Search Report and Written Opinion for PCT/US2011/023278 dated Jul. 18, 2011. (15 pages).
Invitation to Pay Additional Fees and Partial Search Report for PCT/US2011/023331 mailed May 4, 2011.
Written Opinion for PCT/US2011/023278 mailed Jan. 30, 2012.
Invitation to Pay Fees for PCT/US2011/046502 dated Mar. 9, 2012.
International Written Opinion mailed Nov. 8, 2012 in corresponding International Application No. PCT/US2011/046493.
International Preliminary Report on Patentability mailed Jan. 16, 2013 in corresponding International Application No. PCT/US2011/046493.
Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.
ZeaChem, Inc., Technology Overview, Lakewood, Colorado www.zeachem.com, 2008.
Santori et al.(2000). Hydrogenation of carbonylic compounds on Pt/SiO2 catalysts modified with SnBu4, Studies in Surface Science and Catalysis, 130, 2063-2068.
Rachmady, Acetic Acid Reduction by H2 on Bimetallic Pt—Fe Catalysts, Journal of Catalysis 209, 87-98 (Apr. 1, 2002), Elsevier Science (USA).
Pestman et al., Reactions of Carboxylic Acids on Oxides, Journal of Catalysis 168:255-264 (1997).
Pestman et al., Identification of the Active Sites in the Selective Hydrogenation of Acetic Acid to Acetaldehyde on Iron Oxide Catalysts, Journal of Catalysis 174:142-152 (1998).
Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.
Ordóñez et al., The role of metal and support sites on the hydrogenation of acetic acid on Ru-based catalysts, 21st NAM San Francisco, CA, Jun. 10, 2009.
Brunauer Emmett and Teller, J. Am. Chem. Soc. 60, 309 (1938).
Hilmen, Separation of Azeotropic Mixtures: Tools for Analysis and Studies on Batch Distillation Operation (Nov. 2000) p. 17-20.
Gursahani et al., Reaction kinetics measurements and analysis of reaction pathways for conversions of acetic acid, ethanol, and ethyl acetate over silica-supported Pt, Applied Catalysis A: General 222 (2001) 369-392.
Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.
Acala, et al., (2005). Experimental and DFT studies of the conversion of ethanol and acetic acid on PtSn-based catalysts, Journal of Physical Chemistry, 109(6), 2074-2085.
Invitation to Pay Fees for PCT/US2011/046493 dated Feb. 6, 2012.
International Search Report and Written Opinion mailed Oct. 16, 2012 in corresponding International Application No. PCT/US2011/046511.
U.S. Office Action mailed Sep. 4, 2012 in co-pending U.S. Appl. No. 12/852,290.

* cited by examiner

US 8,728,179 B2

ETHANOL COMPOSITIONS

CROSS REFERENCE TO RELATED APPLICATIONS

This application claims priority to U.S. Non-Provisional application Ser. No. 12/852,290, filed on Aug. 6, 2010, which claims priority to U.S. Provisional Application No. 61/300,815, filed on Feb. 2, 2010, U.S. Provisional Application No. 61/332,696, filed on May 7, 2010, U.S. Provisional Application No. 61/332,699, filed on May 7, 2010, U.S. Provisional Application No. 61/332,728, filed on May 7, 2010, and to U.S. Provisional Application No. 61/346,344, filed on May 19, 2010; and to U.S. Non-Provisional application Ser. No. 12/889,260, filed on Sep. 23, 2010, which claims priority to U.S. Provisional Application No. 61/300,815, filed on Feb. 2, 2010, U.S. Provisional Application No. 61/332,727, filed on May 7, 2010, and U.S. Provisional Application No. 61/332,696, the entire contents and disclosures of which are incorporated herein by reference.

FIELD OF THE INVENTION

The present invention relates generally to processes for producing and/or purifying ethanol and, in particular, to ethanol compositions obtained from these processes.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. In addition to petrochemical feed stocks synthesis methods, starchy materials, as well as cellulose materials, may be converted to ethanol by fermentation. Fermentation methods are typically employed for production of consumable ethanol, although the ethanol thus produced may also be suitable for fuels. Fermentation of starchy or cellulose materials also competes with food sources and places restraints on the amount of ethanol that can be produced for industrial use.

Conventional ethanol compositions that are formed as a result of the above-identified processes contain impurities, which must be removed.

For example, U.S. Pat. No. 5,488,185 utilizes a petrochemical feed stock and relates to an ethene stream which contains ethane as an impurity or a propene stream which contains propane as an impurity that is hydrated with water vapor in the presence of a hydration catalyst to produce ethanol or isopropanol, respectively. After removal of the alcohol the gaseous product stream is subjected to adsorption, thereby producing an ethene-enriched stream or a propene-enriched stream. The ethene-enriched stream or the propene-enriched stream is recycled to the hydration reactor.

U.S. Pat. Nos. 5,185,481 and 5,284,983 relate to conventional fermentation methods for producing ethanol. The produced ethanol compositions comprise impurities such as methanol, acetaldehyde, n-propanol, n-butanol, ethyl acetate, 3-methylbutanol, diethyl ether, acetone, secondary butanol, and crotonaldehyde. These references also disclose separation methods for treating the crude ethanol aqueous solution with an extracting solvent comprising carbon dioxide in a liquid state or carbon dioxide in a super-critical state.

U.S. Pat. Nos. 5,445,716; 5,800,681; and 5,415,741 relate to separation methods for mixtures of ethanol and isopropanol. Ethanol is difficult to separate from isopropanol by conventional distillation or rectification because of the proximity of their boiling points. Ethanol can be readily separated from isopropanol by extractive distillation. Effective extractive agents are dipentene, anisole, and ethyl benzene. The mixtures in these references, comprise a significant amount of isopropanol, e.g., at least 21.5 wt. % isopropanol.

Also, U.S. Pat. No. 5,858,031 relates to a method for enhancing the visibility of a flame produced during free-burning of an aqueous alcohol-based fuel composition in air. The fuel includes between approximately 10% and 30% by volume of water, and between approximately 70% and 90% by volume of a mixture of alcohols including ethanol and isopropanol, the ethanol constituting between approximately 24% and 83% by volume of the fuel composition. The method includes providing an amount of isopropanol ranging between approximately 7% and 60% by volume of the fuel composition, in which the volume ratio of isopropanol to ethanol in the fuel does not exceed 2:1.

Although conventional processes may produce and/or purify ethanol compositions, these processes rely on petrochemical feed stocks or fermentation techniques to yield the ethanol compositions. Further, in the resultant ethanol compositions that do comprise isopropanol, the isopropanol is present in large amounts.

Therefore, the need exists for an ethanol production process that does not rely on petrochemical feed stocks, and does not utilize fermentation techniques.

SUMMARY OF THE INVENTION

In one embodiment, the invention is to an ethanol composition. The ethanol composition comprises ethanol, water, and isopropanol. Preferably, the ethanol composition comprises at least 85 wt. % ethanol, less than 12 wt. % water, and from 95 wppm to 850 wppm isopropanol. The ethanol composition has a high degree of purity and may further comprise less than 1 wt. % of one or more organic impurities. These organic impurities may include, for example, acetaldehyde, acetic acid, diethyl acetal, ethyl acetate, n-propanol, butanol, 2-butanol, isobutanol, and mixtures thereof. For example, the ethanol composition may comprise less than 18 wppm acetaldehyde; less than 40 wppm of methanol; and/or less than 55 wppm diethyl. In other embodiments, the ethanol composition is substantially free of benzene, methanol, and/or $C_{5+}$ alcohols. In some embodiments, the ethanol is not derived via fermentation methods.

In one embodiment, the invention is to an ethanol composition comprising diethyl acetal in low amounts. As one example, the inventive ethanol composition comprises diethyl acetal in an amount less than 10 wppm. In another embodiment, the ethanol composition comprises up to 10 wppm diethyl acetal.

In one embodiment, the invention is to an ethanol composition comprises ethanol, isopropanol and diethyl acetal. Preferably, the ethanol composition comprises at least 85 wt. % ethanol; from 95 wppm to 850 wppm isopropanol; and less than 10 wppm diethyl acetal. In an embodiment, the ethanol composition comprises from 85 wt. % to 99 wt. % ethanol. Preferably, the ethanol composition may comprise less than 40 wppm methanol, less than 18 wppm acetaldehyde, and/or less than 22 wppm $C_4$-$C_5$ alcohols. In one embodiment, the composition may be derived from the hydrogenation of acetic acid.

In one embodiment, the invention is to an ethanol composition comprises ethanol and acetone. The ethanol composition preferably comprises at least 85 wt. % ethanol and from 50 wppm to 500 wppm acetone. The ethanol composition may comprise less than 10 wppm diethyl acetal and/or less than 18 wppm acetaldehyde. Preferably, the ethanol composition is derived from hydrogenation of acetic acid.

In another embodiment, the invention is to an ethanol composition comprises ethanol, isopropanol and $C_4$-$C_5$ alcohols. Preferably, the ethanol composition comprises at least 85 wt. % ethanol, from 95 wppm to 850 wppm isopropanol, and less than 30 wppm $C_4$-$C_5$ alcohols. The ethanol composition may comprise up to 10 wppm diethyl acetal.

In another embodiment, the invention is to an ethanol composition comprises ethanol, at least one denaturant, and isopropanol. Preferably, the ethanol composition comprises from 50 wt. % to 99 wt. % ethanol, at least 1 wt. % of at least one denaturant selected from the group consisting of ethyl acetate, acetaldehyde, acetone, acetal, and n-propanol, and from 95 wppm to 850 wppm isopropanol. Preferably, the denaturant is an in situ denaturant. The ethanol composition may comprise less than 50 wppm of a combination of methanol and $C_{6+}$ alcohols. The ethanol may be substantially free of $C_{6+}$ alcohols.

In another embodiment, the invention is to an ethanol composition produced directly from acetic acid by the carbonylation reaction of methanol. Preferably, the ethanol composition comprises at least 85 wt. % ethanol, from 95 to 850 wppm isopropanol and less than 100 wppm n-propanol.

In another embodiment, the invention is to an ethanol composition synthesized via hydrogenation and purified using at least one distillation column. Preferably, the ethanol composition comprises at least 85 wt. % ethanol, from 95 wppm to 850 wppm isopropanol and less than 10 wppm diethyl acetal.

In another embodiment, the invention is to a synthesized ethanol composition. Preferably, the ethanol composition comprises at least 85 wt. % ethanol, from 95 wppm to 850 wppm isopropanol and less than 20 wppm butanol.

BRIEF DESCRIPTION OF DRAWINGS

The invention is described in detail below with reference to the appended drawings, wherein like numerals designate similar parts.

DETAILED DESCRIPTION OF THE INVENTION

The present invention relates to processes for recovering a finished ethanol composition from, e.g. a crude ethanol product produced by a hydrogenation process. In one embodiment, the hydrogenation process comprises the step of hydrogenating acetic acid in the presence of a catalyst. The hydrogenation process produces a crude ethanol product that is different from the crude ethanol composition produced by other ethanol production processes. For example, fermentation processes produce crude ethanol compositions having low ethanol content. Crude ethanol compositions produced from petrochemical feed stocks produces crude ethanol compositions comprising other alcohols, especially methanol, n-propanol and higher alcohols. As another example, Fischer-Tropsch synthesis has conventionally been employed to make hydrocarbons such as ethanol from coal, natural gas, and biomass. This process, however, has a high catalyst deactivation rate and requires the clean-up of synthetic gas by-products. Also, ethanol synthesized via Fischer-Tropsch methods may often contain higher amounts of methanol and/or higher alcohols, which may be difficult to remove therefrom. Hydrogenation of acetic acid advantageously produces a unique crude ethanol product. A finished ethanol composition may be recovered therefrom using one or more distillation columns.

The inventive ethanol composition, in one embodiment, comprises a major portion of ethanol, less than 12 wt. % water, and a minor portion of impurities, such as isopropanol, n-propanol, butanol, acetaldehyde, methanol, diethyl acetal, $C_4$ alcohol, $C_5$ alcohol, $C_{6+}$ alcohols. In one embodiment a major portion is defined as more than 50 wt. %, e.g., more than 75 wt. %, more than 90 wt. %, or more than 92 wt. %. A minor portion may be defined as less than 1 wt. %, e.g., less than 0.5 wt. % or less than 0.1 wt. %.

The ethanol composition, in some embodiments, comprises primarily ethanol. For example the ethanol composition may contain from 85 wt. % to 99 wt. % ethanol, e.g., from 90 wt. % to 96 wt. %, or from 92 wt. % to 96 wt. %. Preferably, the ethanol composition comprises at least 85 wt. % ethanol, e.g., at least 90 wt. %, or at least 92 wt. %. Higher amounts of ethanol, for example when an anhydrous ethanol composition is desired, may be possible by further removing the water of the ethanol composition.

In some embodiments, water is present in amount ranging from 3 wt. % to 12 wt. %, e.g., from 4 wt. % to 10 wt. % or from 5 wt. % to 8 wt. %. In terms of upper limits, in one embodiment, the ethanol composition comprises less than 12 wt. % water, e.g., less than 10 wt. %, less than 8 wt. %, or less than 5 wt. %. In terms of lower limits, in one embodiment, the ethanol composition comprises at least 3 wt. % water, at least 4 wt. %, or at least 5 wt. %.

Figure 3:
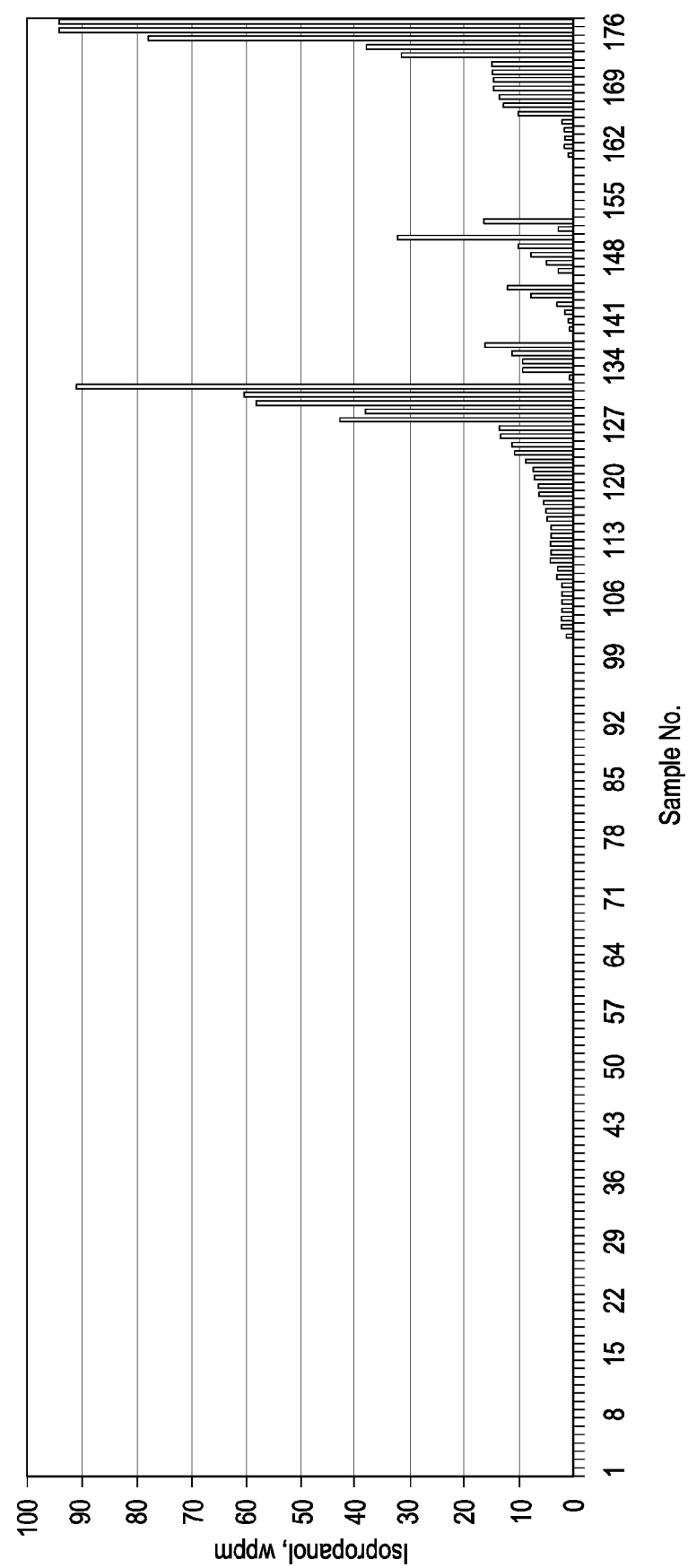
FIG. 3 is a graph displaying isopropanol contents for several conventional ethanol compositions.

In preferred embodiments, isopropanol is present, e.g., in amounts ranging from 95 wppm to 850 wppm, from 110 wppm to 750 wppm, or from 130 wppm to 400 wppm. In other embodiments, the lower end of the range is extended, for example, the isopropanol may be present in an amount ranging from 1 wppm to 850 wppm, e.g., from 10 wppm to 850 wppm. In terms of lower limits, in one embodiment, the ethanol composition comprises at least 1 wppm isopropanol, e.g., at least 10 wppm, at least 95 wppm, at least 110 wppm or at least 150 wppm. In terms of upper limits, in one embodiment, the ethanol composition comprises less than 850 wppm isopropanol, e.g., less than 800 wppm or less than 400 wppm. FIG. 3 displays isopropanol levels of 176 conventional ethanol compositions. These ethanol compositions were derived from various conventional sources and techniques such as sugarcane fermentation, molasses fermentation, and Fischer-Tropsch synthesis. As shown in FIG. 3, each of these conventional ethanol compositions has a very low isopropanol concentration, and none comprise isopropanol in an amount greater than 94 wppm.

In another embodiment, the weight ratio of isopropanol to water in the ethanol composition ranges from 1:80 to 1:800, e.g. from 1:100 to 1:500. In one embodiment, the ethanol composition comprises essentially no other detectable compounds, such as methanol, benzene, and/or higher alcohols, e.g., $C_{4+}$ alcohols. In some embodiments, the ethanol composition may comprise minor amounts of other impurities, such as those described below in Table 7.

In another embodiment, the invention is to an ethanol composition comprising ethanol and at least two other alcohols. The at least two other alcohols may be selected from the group consisting of n-propanol, isopropanol, butanol, 2-butanol, isobutanol, $C_5$ alcohols (collectively), and $C_{6+}$ alcohols (collectively). Preferably, one of the at least two other alcohols is isopropanol. In these embodiments, the isopropanol is present in the amounts discussed above. In preferred embodiments, when the weight percentages of the at least two other alcohols are added together, the at least two other alcohols, collectively, are present in an amount of less than 1 wt. %.

Without being bound by theory, it is believed that isopropanol is formed during the hydrogenation of acetic acid. For example, the isopropanol may be formed via the hydrogenation of acetone. The acetone may be generated via an acetic acid ketonization reaction, which, optionally, may proceed concurrently with the acetic acid hydrogenation. In one embodiment of the present invention, the ethanol composition and/or the acetic acid hydrogenation mixture may comprise acetone, which may be generated as some of the acetic acid from the feed stream is ketonized. Without being bound by theory, it is believed that at least some of the acetone that is present in the ethanol composition and/or the acetic acid hydrogenation reaction mixture may undergo hydrogenation, e.g., acetone hydrogenation, to form isopropanol. In some embodiments, acetone is present in the ethanol composition and/or the acetic acid hydrogenation reaction mixture in an amount less than 500 wppm, e.g., less than 100 wppm, or less than 50 wppm. In terms of ranges, the ethanol composition and/or the acetic acid hydrogenation reaction mixture may comprise from 10 wppm to 500 wppm acetone, e.g., from 30 wppm to 400 wppm acetone, or from 50 wppm to 300 wppm acetone. At least a portion of the acetone in the ethanol composition and/or the acetic acid hydrogenation reaction mixture may or may not hydrogenate to form isopropanol. Preferably, a portion of the acetone yields isopropanol. Further, in one embodiment, the weight ratio of isopropanol to acetone in the inventive ethanol composition may range from 1:20 to 10:1, e.g., from 1:15 to 5:1, from 1:10 to 1:1, or from 1:5 to 0.1. In terms of limits, the weight ratio of isopropanol to acetone may be at least 1:5, e.g., at least 1:10, at least 1:15, or at least 1:20.

The n-propanol, if present in the ethanol composition, is believed to be formed from impurities in the acetic acid feed. The ethanol compositions of the present invention preferably comprise n-propanol in an amount less than 0.5 wt. % n-propanol, e.g., less than 0.1 wt. % or less than 0.05 wt. %. Optionally, the ethanol compositions of the present invention may preferably have less n-propanol than isopropanol.

The ethanol compositions formed by the inventive processes comprise a higher amount of in situ-formed isopropanol than conventional ethanol compositions. Preferably, in the inventive ethanol compositions, the amount of n-propanol is less than the amount of isopropanol, e.g., less than 10% the amount of isopropanol or less than 50% the amount of isopropanol. Further, in one embodiment, the weight ratio of isopropanol to n-propanol in the inventive ethanol composition may range from 0.1:1 to 10:1, e.g., from 0.5:1 to 10:1, from 1:1 to 5:1, or from 1:1 to 2:1. In terms of limits, the weight ratio of isopropanol to n-propanol may be at least 0.5:1, e.g., at least 1:1, at least 1.5:1, at least 2:1, at least 5:1 or at least 10:1. In conventional ethanol production processes, isopropanol is typically not present in the amounts discussed above. Thus, the weight ratio of isopropanol or n-propanol favors more n-propanol, e.g., greater than 10:1.

In one embodiment of the present invention, isopropanol preferably is not added to the finished ethanol composition after the separation and recovery of ethanol. The isopropanol formed during the hydrogenation of acetic acid may be carried with the ethanol through the separation process.

In addition, conventional hydrogenation reactions often form higher amounts of acetaldehyde, as compared to isopropanol. The inventive ethanol compositions comprise low amounts of acetaldehyde, as well as other acetal compounds. Preferably, in the inventive ethanol compositions, acetaldehyde is present in an amount of less than 18 wppm, e.g., less than 10 wppm, or less than 5 wppm. Preferably, in the inventive ethanol compositions, the amount of acetaldehyde is less than the amount of isopropanol. For example, the amount of acetaldehyde may be less than 50% of the amount of isopropanol, e.g., less than 10% of the amount of isopropanol or less than 5% of the amount of isopropanol. Further the weight ratio of isopropanol to acetaldehyde in the inventive ethanol composition may range from 1:100 to 1:1000, e.g., from 1:100 to 1:500.

In one embodiment, the ethanol composition of the present invention comprises minor amounts of organic impurities. These organic impurities may include acetaldehyde, acetic acid, diethyl acetal, ethyl acetate, n-propanol, methanol, butanol, 2-butanol, isobutanol, isoamyl alcohol, amyl alcohol, benzene and/or mixtures thereof. Beneficially, in one embodiment, the ethanol composition comprises less than 1 wt. % organic impurities, e.g., less than 0.75 wt. % or less than 0.5 wt. %. In preferred embodiments, the ethanol composition comprises less than 0.75 wt. % of impurities that are alcohols, e.g. less than 0.5 wt. %, or less than 0.1 wt. % Depending on the amount of organic impurities, the impurities may have detrimental effects on the resultant ethanol composition. For example, other alcohols in the crude ethanol composition may esterify with the acetic acid to form other esters. Also, it has been found that isobutanol, iso-amyl alcohol, and 2-methyl-1-butanol ("active amyl alcohol") contribute to residual odor in ethanol and ethyl acetate compositions. Beneficially, the inventive ethanol compositions comprise low amounts of these organic impurities. As a result, the detrimental effects thereof are reduced.

In preferred embodiments, the ethanol composition is substantially methanol-free. In one embodiment, the ethanol composition may comprise less than 40 wppm methanol, e.g., less than 10 wppm, or less than 1 wppm. In preferred embodiments, the ethanol composition is substantially free of butanol. In one embodiment, the ethanol composition may comprise less than 20 wppm butanol, e.g., less than 10 wppm butanol, or free of butanol. In one embodiment, the ethanol composition is substantially free of 2-butanol. In one embodiment, the ethanol composition comprises less than 80 wppm 2-butanol, e.g. less than 8 wppm 2-butanol. In addition, in preferred embodiments, the ethanol composition is substantially free of $C_5$ alcohols. In one embodiment, the ethanol composition may comprise less than 10 wppm of $C_5$ alcohols, e.g., less than 1 wppm. In preferred embodiments, the ethanol composition is substantially free of $C_{6+}$ alcohols. In one embodiment, the ethanol composition may comprise less than 10 wppm of $C_5$ alcohols, e.g., less than 1 wppm. In addition, in preferred embodiments, the ethanol composition is substantially free of $C_5$ alcohols. In one embodiment, the ethanol composition may comprise less than 10 wppm of $C_5$ alcohols, e.g., less than 1 wppm. In preferred embodiments, the ethanol composition is substantially free of $C_{6+}$ alcohols. In one embodiment, the ethanol composition may comprise less than 10 wppm of $C_{6+}$ alcohols, e.g., less than 1 wppm.

Without being bound by theory, it is believed that diethyl acetal is generated when ethanol reacts with acetaldehyde in the acetic acid hydrogenation reaction mixture. Acetaldehyde may be an intermediate in this hydrogenation process. Diethyl acetal, if present in the ethanol composition, is present in an amount less than 10 wppm, e.g., less than 5 wppm, or less than 2 wppm. In terms of ranges, the ethanol composition may comprise from 0.1 wppm to 10 wppm diethyl acetal, e.g., from 2 wppm to 8 wppm, or from 2 wppm to 5 wppm.

In one embodiment, the ethanol composition comprises at least one denaturant that is co-produced with the ethanol. For example, the denaturant(s) are formed as a by-product of the hydrogentation reaction. In other words, the denaturant is formed in situ with the ethanol. The ethanol composition may include denaturants, such as ethyl acetate, acetaldehyde, acetone, acetal, and n-propanol. Preferably, the ethanol composition comprises from 50 wt. % to 99 wt. % ethanol and at least 1 wt. % of denaturants, where the denaturants do not include isopropanol. The ethanol composition may also comprises from 95 wppm to 850 wppm isopropanol.

Benzene, dioxanes, and cyanides are known to present toxicity issues in ethanol compositions. Typically, cyanides result from fermentation methods that utilize cassava as a feed stock. The inventive ethanol compositions comprise low amounts of these components. Preferably, the ethanol composition contains no detectable amount of benzene, dioxanes, and cyanides.

Hydrogenation Process

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming syngas, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as a syngas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol a variety of configuration using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of: cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $CO_2O_3$, $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group JIB metal oxides, (vi) Group JIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain N or Pro. The Saint-Gobain N or Pro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%.

Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram catalyst per hour or from 600 to 2,000 grams of ethanol per kilogram catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. In some exemplary embodiments, the crude ethanol product comprises ethanol in an amount from 5 to 70 wt. %, e.g., from 10 to 60 wt. %, or from 15 to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid optionally is present in the crude ethanol product in an amount from 0 to 90 wt. %, e.g., from 5 to 80 wt. %, from 15 to 70 wt. %, from 20 to 70 wt. % or from 25 to 65 wt. %. As water is formed in the reaction process, water will generally be present in the crude ethanol product, for example, in amounts ranging from 5 to 40 wt. %, e.g., from 10 to 30 wt. % or from 10 to 26 wt. %.

Ethyl acetate may also be produced during the hydrogenation of acetic acid or through side reactions and may be present, for example, in amounts ranging from 0 to 30 wt. %, e.g., from 0 to 20 wt. %, from 1 to 12 wt. % or from 3 to 10 wt. %. Acetaldehyde may also be produced through side reactions and may be present, for example, in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, ketones, alkanes, and carbon dioxide, if detectable, collectively may be present in amounts less than 10 wt. %, e.g., less than 6 wt. % or less than 4 wt. %. In terms of ranges, other components may be present in an amount from 0.1 to 10 wt. %, e.g., from 0.1 to 6 wt. %, or from 0.1 to 4 wt. %. Exemplary component ranges for the crude ethanol product are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 80 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 50%, e.g., greater than 75% or greater than 90%. In addition, the selectivity to ethanol may also be preferably high, and is preferably greater than 50%, e.g., greater than 75% or greater than 90%.

Purification

Figure 1:
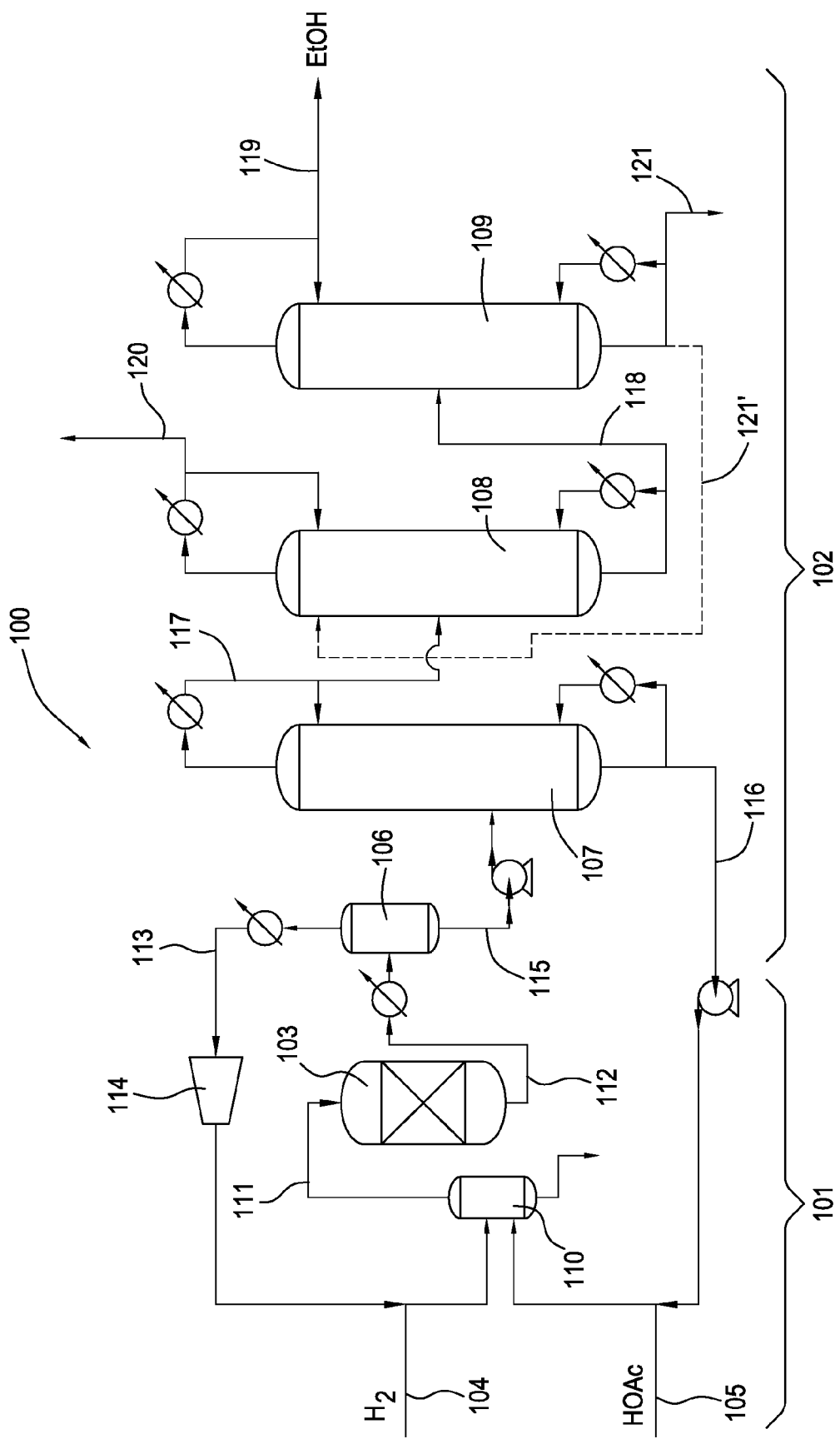
FIG. 1 is a schematic diagram of a hydrogenation system in accordance with one embodiment of the present invention.

FIG. 1 shows a hydrogenation system 100 suitable for the hydrogenation of acetic acid and separating ethanol from the crude reaction mixture according to one embodiment of the invention. System 100 comprises reaction zone 101 and distillation zone 102. Reaction zone 101 comprises reactor 103, hydrogen feed line 104 and acetic acid feed line 105. Distillation zone 102 comprises flasher 106, first column 107, second column 108, third column 109, and fourth column 123. Hydrogen and acetic acid are fed to a vaporizer 110 via lines 104 and 105, respectively, to create a vapor feed stream in line 111 that is directed to reactor 103. In one embodiment, lines 104 and 105 may be combined and jointly fed to the vaporizer 110, e.g., in one stream containing both hydrogen and acetic acid. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIG. 1, and may be recycled thereto. In addition, although FIG. 1 shows line 111 being directed to the top of reactor 103, line 111 may be directed to the side, upper portion, or bottom of reactor 103. Further modifications and additional components to reaction zone 101 are described below in FIG. 2.

Reactor 103 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product is withdrawn, preferably continuously, from reactor 103 via line 112. The crude ethanol product may be condensed and fed to flasher 106, which, in turn, provides a vapor stream and a liquid stream. The flasher 106 in one embodiment preferably operates at a temperature of from 50° C. to 500° C., e.g., from 70° C. to 400° C. or from 100° C. to 350° C. In one embodiment, the pressure of flasher 106 preferably is from 50 kPa to 2000 kPa, e.g., from 75 kPa to 1500 kPa or from 100 to 1000 kPa. In one preferred embodiment the temperature and pressure of the flasher is similar to the temperature and pressure of the reactor 103.

The vapor stream exiting the flasher 106 may comprise hydrogen and hydrocarbons, which may be purged and/or returned to reaction zone 101 via line 113. As shown in FIG. 1, the returned portion of the vapor stream passes through compressor 114 and is combined with the hydrogen feed and co-fed to vaporizer 110.

The liquid from flasher 106 is withdrawn and pumped as a feed composition via line 115 to the side of first column 107, also referred to as the acid separation column. The contents of line 115 typically will be substantially similar to the product obtained directly from the reactor, and may, in fact, also be characterized as a crude ethanol product. However, the feed composition in line 115 preferably has substantially no hydrogen, carbon dioxide, methane or ethane, which are removed by flasher 106. Exemplary components of liquid in line 115 are provided in Table 2. It should be understood that liquid line 115 may contain other components, not listed, such as components in the feed.

TABLE 2

FEED COMPOSITION

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 115, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

When the content of acetic acid in line 115 is less than 5 wt. %, the acid separation column 107 may be skipped and line 115 may be introduced directly to second column 108, also referred to herein as a light ends column.

In the embodiment shown in FIG. 1, line 115 is introduced in the lower part of first column 107, e.g., lower half or lower third. In first column 107, unreacted acetic acid, a portion of the water, and other heavy components, if present, are removed from the composition in line 115 and are withdrawn, preferably continuously, as residue. Some or all of the residue may be returned and/or recycled back to reaction zone 101 via line 116. First column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

Any of columns 107, 108, 109, or 123 may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIG. 1. As shown in FIG. 1, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and one flasher are shown in FIG. 1, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 kPa to 3000 kPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependent on the composition of the material at that location and the pressure of column. In addition, feed rates may vary depending on the size of the production process and, if described, may be generically referred to in terms of feed weight ratios.

When column 107 is operated under standard atmospheric pressure, the temperature of the residue exiting in line 116 from column 107 preferably is from 95° C. to 120° C., e.g., from 105° C. to 117° C. or from 110° C. to 115° C. The temperature of the distillate exiting in line 117 from column 107 preferably is from 70° C. to 110° C., e.g., from 75° C. to 95° C. or from 80° C. to 90° C. In other embodiments, the pressure of first column 107 may range from 0.1 kPa to 510 kPa, e.g., from 1 kPa to 475 kPa or from 1 kPa to 375 kPa. Exemplary components of the distillate and residue compositions for first column 107 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN

|  | Conc. (wt. %) | Conc. (wt. %) | Conc. (wt. %) |
|---|---|---|---|
| Distillate |  |  |  |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

Depending on the reaction conditions, the crude ethanol product exiting reactor 103 in line 112 may comprise ethanol, acetic acid (unconverted), ethyl acetate, and water. After exiting reactor 103, a non-catalyzed equilibrium reaction may occur between the components contained in the crude ethanol product until it is added to flasher 106 and/or first column 107. This equilibrium reaction tends to drive the crude ethanol product to an equilibrium between ethanol/acetic acid and ethyl acetate/water, as shown below.

EtOH+HOAc⇌EtOAc+H₂O

In the event the crude ethanol product is temporarily stored, e.g., in a holding tank, prior to being directed to distillation zone 102, extended residence times may be encountered. Generally, the longer the residence time between reaction zone 101 and distillation zone 102, the greater the formation of ethyl acetate. For example, when the residence time between reaction zone 101 and distillation zone 102 is greater than 5 days, significantly more ethyl acetate may form at the expense of ethanol. Thus, shorter residence times between reaction zone 101 and distillation zone 102 are generally preferred in order to maximize the amount of ethanol formed. In one embodiment, a holding tank (not shown), is included between the reaction zone 101 and distillation zone 102 for temporarily storing the liquid component from line 115 for up to 5 days, e.g., up to 1 day, or up to 1 hour. In a preferred embodiment no tank is included and the condensed liquids are fed directly to the first distillation column 107. In addition, the rate at which the non-catalyzed reaction occurs may increase as the temperature of the crude ethanol product, e.g., in line 115, increases. These reaction rates may be particularly problematic at temperatures exceeding 30° C., e.g., exceeding 40° C. or exceeding 50° C. Thus, in one embodiment, the temperature of liquid components in line 115 or in the optional holding tank is maintained at a temperature less than 40° C., e.g., less than 30° C. or less than 20° C. One or more cooling devices may be used to reduce the temperature of the liquid in line 115.

As discussed above, a holding tank (not shown) may be included between the reaction zone 101 and distillation zone 102 for temporarily storing the liquid component from line 115, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude ethanol product is increased. For example, as the temperature of the crude ethanol product in line 115 increases from 4° C. to 21° C., the rate of ethyl acetate formation may increase from about 0.01 wt. % per hour to about 0.005 wt. % per hour. Thus, in one embodiment, the temperature of liquid components in line 115 or in the optional holding tank is maintained at a temperature less than 21° C., e.g., less than 4° C. or less than −10° C.

In addition, it has now been discovered that the above-described equilibrium reaction may also favor ethanol formation in the top region of first column 107.

The distillate, e.g., overhead stream, of column 107 optionally is condensed and refluxed as shown in FIG. 1, preferably, at a reflux ratio of 1:5 to 10:1. The distillate in line 117 preferably comprises ethanol, ethyl acetate, and water, along with other impurities, which may be difficult to separate due to the formation of binary and tertiary azeotropes.

The first distillate in line 117 is introduced to the second column 108, also referred to as the "light ends column," preferably in the middle part of column 108, e.g., middle half or middle third. As one example, when a 25 tray column is utilized in a column without water extraction, line 117 is introduced at tray 17. In one embodiment, the second column 108 may be an extractive distillation column. In such embodiments, an extraction agent, such as water, may be added to second column 108. If the extraction agent comprises water, it may be obtained from an external source or from an internal return/recycle line from one or more of the other columns.

Second column 108 may be a tray column or packed column. In one embodiment, second column 108 is a tray column having from 5 to 70 trays, e.g., from 15 to 50 trays or from 20 to 45 trays.

Although the temperature and pressure of second column 108 may vary, when at atmospheric pressure the temperature of the second residue exiting in line 118 from second column 108 preferably is from 60° C. to 90° C., e.g., from 70° C. to 90° C. or from 80° C. to 90° C. The temperature of the second distillate exiting in line 120 from second column 108 preferably is from 50° C. to 90° C., e.g., from 60° C. to 80° C. or from 60° C. to 70° C. Column 108 may operate at atmospheric pressure. In other embodiments, the pressure of second column 108 may range from 0.1 kPa to 510 kPa, e.g., from 1 kPa to 475 kPa or from 1 kPa to 375 kPa. Exemplary components for the distillate and residue compositions for second column 108 are provided in Table 4 below. It should be understood that the distillate and residue may also contain other components, not listed, such as components in the feed.

TABLE 4

SECOND COLUMN

|  | Conc. (wt. %) | Conc. (wt. %) | Conc. (wt. %) |
|---|---|---|---|
| Distillate |  |  |  |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 30 to 70 | 30 to 60 | 30 to 50 |
| Ethanol | 20 to 75 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate approaches zero.

As shown, the second residue from the bottom of second column 108, which comprises ethanol and water, is fed via line 118 to third column 109, also referred to as the "product column." More preferably, the second residue in line 118 is introduced in the lower part of third column 109, e.g., lower half or lower third. Third column 109 recovers ethanol, which preferably is substantially pure other than the azeotropic water content, as the distillate in line 119. The distillate of third column 109 preferably is refluxed as shown in FIG. 1, for example, at a reflux ratio of from 1:10 to 10:1, e.g., from 1:3 to 3:1 or from 1:2 to 2:1. The third residue in line 121, which preferably comprises primarily water, preferably is removed from the system 100 or may be partially returned to any portion of the system 100. Third column 109 is preferably a tray column as described above and preferably operates at atmospheric pressure. The temperature of the third distillate exiting in line 119 from third column 109 preferably is from 60° C. to 110° C., e.g., from 70° C. to 100° C. or from 75° C. to 95° C. The temperature of the third residue exiting from third column 109 preferably is from 70° C. to 115° C., e.g., from 80° C. to 110° C. or from 85° C. to 105° C., when the column is operated at atmospheric pressure. Exemplary components of the distillate and residue compositions for third column 109 are provided in Table 5 below. It should be understood that the distillate and residue may also contain other components, not listed, such as components in the feed.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 99.9 | 80 to 99.9 | 85 to 99.9 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |

TABLE 5-continued

THIRD COLUMN

|  | Conc. (wt. %) | Conc. (wt. %) | Conc. (wt. %) |
|---|---|---|---|
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

The ethanol composition may comprise the impurities, e.g., organic impurities, discussed above. The ethanol composition, in some embodiments, may further comprise other compounds that result from the reaction or separation processes. These other compounds may be carried through the distillation process from the feed or crude reaction product may generally remain in the third distillate in small amounts. For example, the other compounds may be present in amounts less 0.1 wt. %, based on the total weight of the third distillate composition, e.g., less than 0.05 wt. % or less than 0.02 wt. %. In one embodiment, one or more side streams may remove impurities from any of the columns 107, 108 and/or 109 in the system 100. Preferably at least one side stream is used to remove impurities from the third column 109. The impurities may be purged and/or retained within the system 100.

The third distillate in line 119 may be further purified to form an anhydrous ethanol product stream, e.g., "finished anhydrous ethanol," using one or more additional separation systems, such as, for example, distillation columns (e.g., a finishing column) or molecular sieves.

Returning to second column 108, the second distillate preferably is refluxed as shown in FIG. 1, for example, at a reflux ratio of from 1:10 to 10:1, e.g., from 1:5 to 5:1 or from 1:3 to 3:1. The second distillate may be fed via line 120 to fourth column 123, also referred to as the "acetaldehyde removal column." In fourth column 123 the second distillate is separated into a fourth distillate, which comprises acetaldehyde, in line 124 and a fourth residue, which comprises ethyl acetate, in line 125. The fourth distillate preferably is refluxed at a reflux ratio of from 1:20 to 20:1, e.g., from 1:15 to 15:1 or from 1:10 to 10:1, and a portion of the fourth distillate is returned to the reaction zone 101 as shown by line 124. For example, the fourth distillate may be combined with the acetic acid feed, added to the vaporizer 110, or added directly to the reactor 103. As shown, the fourth distillate is co-fed with the acetic acid in feed line 105 to vaporizer 110. Without being bound by theory, since acetaldehyde may be hydrogenated to form ethanol, the recycling of a stream that contains acetaldehyde to the reaction zone increases the yield of ethanol and decreases byproduct and waste generation. In another embodiment (not shown in the figure), the acetaldehyde may be collected and utilized, with or without further purification, to make useful products including but not limited to n-butanol, 1,3-butanediol, and/or crotonaldehyde and derivatives.

The fourth residue of fourth column 123 may be purged via line 125. The fourth residue primarily comprises ethyl acetate and ethanol, which may be suitable for use as a solvent mixture or in the production of esters. In one preferred embodiment, the acetaldehyde is removed from the second distillate in fourth column 123 such that no detectable amount of acetaldehyde is present in the residue of column 123.

Fourth column 123 is preferably a tray column as described above and preferably operates above atmospheric pressure. In one embodiment, the pressure is from 120 kPa to 5,000 kPa, e.g., from 200 kPa to 4,500 kPa, or from 400 kPa to 3,000 kPa.

In a preferred embodiment the fourth column 123 may operate at a pressure that is higher than the pressure of the other columns.

The temperature of the fourth distillate exiting in line 124 from fourth column 123 preferably is from 60° C. to 110° C., e.g., from 70° C. to 100° C. or from 75° C. to 95° C. The temperature of the residue exiting from fourth column 125 preferably is from 70° C. to 115° C., e.g., from 80° C. to 110° C. or from 85° C. to 110° C. Exemplary components of the distillate and residue compositions for fourth column 123 are provided in Table 6 below. It should be understood that the distillate and residue may also contain other components, not listed, such as components in the feed.

TABLE 6

FOURTH COLUMN

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

Figure 2:
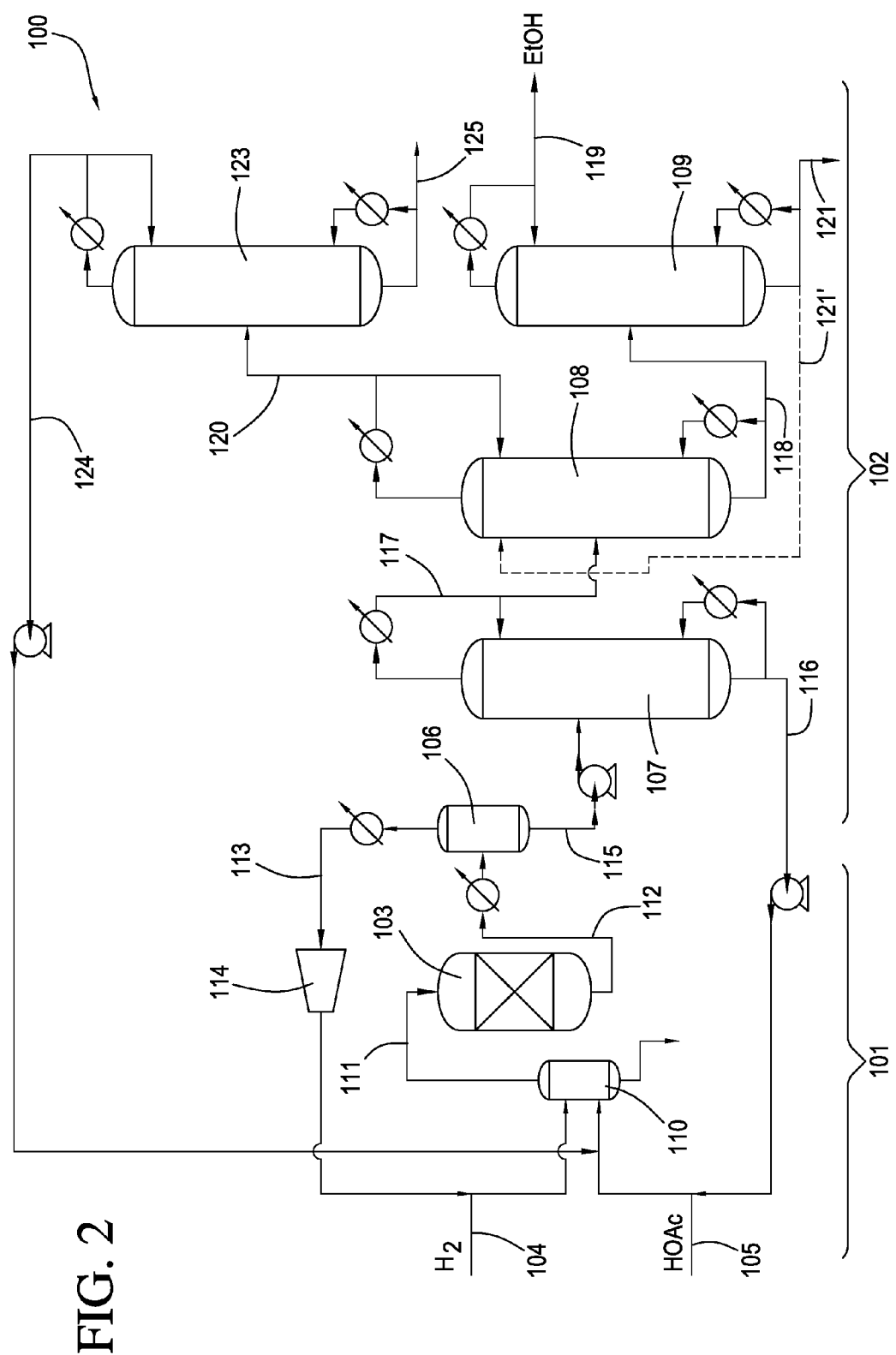
FIG. 2 is a schematic diagram of the reaction zone in accordance with one embodiment of the present invention.

Although one reactor and one flasher are shown in FIG. 1, additional reactors and/or components may be included in various optional embodiments of the present invention. FIG. 2 represents a hydrogenation system 100' that comprises dual reactors 103, 103', dual flashers 106, 106', heat exchanger 130, and pre-heater 131. In this embodiment, acetic acid in line 105, along with the recycled acetic acid in line 116 and recycled acetaldehyde from line 124, are heated in a heat exchanger 130 and sent to vaporizer 110 via line 132. The temperature of the contents of line 132 preferably is from 30° C. to 150° C., e.g., from 50° C. to 130° C. or from 75° C. to 120° C. Hydrogen is fed via line 104 to vaporizer 110, which forms vaporized stream 111. Vaporized stream 111 passes through pre-heater 131, which further heats stream 111 to a temperature of preferably from 200° C. to 300° C., e.g., from 210° C. to 275° C. or from 220° C. to 260° C. The heated stream is then fed to first reactor 103. In order to control the reaction exotherm, the crude reaction mixture is removed from first reactor 103 via line 133 and cooled before being fed to a second reactor 103', such that the temperature of the reactants and products in contact with the catalyst is maintained at or below 310° C. in order to minimize the formation of undesired byproducts including methane, ethane, carbon dioxide, and/or carbon monoxide. Additionally, above about 320° C. corrosion can become severe necessitating the use of exotic and expensive alloy materials. The temperature of the contents in line 133 after cooling preferably is from 200° C. to 300° C., e.g., from 210° C. to 275° C. or from 220° C. to 260° C. The reactors 103 and 103' may be the same size and configuration or they may be of different size and configuration. Each reactor preferably contains the same type of catalyst, although additional and/or different catalysts may be used for each reactor. As an example, the catalysts mentioned above may be utilized. Also, mixtures of catalysts, mixtures of catalysts and inert materials, and/or catalysts with differing active metal concentrations may be utilized. For example, the catalyst may include the same types of metal in varying metal ratios. A crude ethanol product is withdrawn, preferably continuously, from reactor 103' via line 112 and passes as a heating medium through heat exchanger 130 before being condensed and fed to first flasher 106. Thus, heat from the crude ethanol product advantageously may be employed to preheat the acetic acid feed prior to its introduction into vaporizer 110. Conversely, the acetic acid feed may be used as a cooling medium to cool the crude ethanol product prior to its introduction to first flasher 106. The vapor stream exiting the first flasher comprises hydrogen and hydrocarbons, which may be purged and/or returned to reaction zone 101 via line 113. As shown in FIG. 2, at least a portion of the recycled vapor stream passes through compressor 114 and is co-fed with the hydrogen (or combined with hydrogen and then co-fed) to vaporizer 110.

The remaining liquid in flasher 106 is withdrawn via line 134 and fed to a second flasher 106' to remove any residual vapor that is dissolved in the liquid. Second flasher 106' may operate at a lower temperature and/or pressure than the first flasher 106. In one embodiment, the temperature of second flasher 106' preferably is from 20° C. to 100° C., e.g., from 30° C. to 85° C. or from 40° C. to 70° C. In one embodiment, the temperature of second flasher 106' preferably is at least 50° C. lower than first flasher 106, e.g., at least 75° C. lower or at least 100° C. lower. The pressure of second flasher 106' preferably is from 0.1 kPa to 1000 kPa, e.g., from 0.1 kPa to 500 kPa or from 0.1 kPa to 100 kPa. In one embodiment, the pressure of second flasher 106' preferably is at least 50 kPa lower than first flasher 106, e.g., at least 100 kPa lower or at least 200 kPa lower. The vapor stream 135 exiting the second flasher may comprise hydrogen and hydrocarbons, which may be purged and/or returned to the reaction zone in a manner similar to that of the first flasher 106. The remaining liquid in flasher 106' is withdrawn and pumped via line 115 to the side of the first column (not shown in FIG. 2) and is further purified to form an ethanol product stream, i.e., "finished ethanol," as described, for example, in connection with FIG. 1.

Finished Ethanol Composition

The finished ethanol compositions obtained by the processes of the present invention preferably comprise ethanol, water, and minor amounts of isopropanol. As indicated above, preferably, the ethanol composition is primarily ethanol and contains from 85 wt. % to 96 wt. % ethanol, e.g., from 90 wt. % to 96 wt. %, or from 92 wt. % to 96 wt. %. In addition, the amount of isopropanol in the ethanol composition may range from 95 wppm to 850 wppm, e.g., from 110 wppm to 800 wppm, or from 110 wppm to 400 wppm.

In another embodiment, the ethanol composition comprises less than 270 wppm n-propanol, e.g., less than 200 wppm. In terms of ranges, the ethanol composition comprises from 95 wppm to 270 wppm n-propanol, e.g., from 100 wppm to 250 wppm, or from 120 wppm to 200 wppm. In preferred embodiments, the ethanol compositions the total amount of isopropanol and n-propanol is less than 1,000 wppm, generally, e.g., less than 400 wppm or less than 200 wppm.

In another embodiment, the ethanol composition comprises water in the amounts discussed above.

In one embodiment, the ethanol composition comprises less than 1 wt. % organic impurities, e.g., less than 0.75 wt. % or less than 0.5 wt. %. In preferred embodiments, the ethanol composition comprises less than 0.75 wt. % alcohol impurities, e.g., less than 0.5 wt. % alcohol impurities, or less than 0.1 wt. % alcohol impurities.

In some embodiments, diethyl acetal, if present in the ethanol composition, is present in an amount less than 10 wppm, e.g., less than 5 wppm, or less than 2 wppm. In terms of ranges, the ethanol composition may comprise from 0.1 wppm to 10 wppm diethyl acetal, e.g., from 2 wppm to 8 wppm diethyl acetal, or from 2 wppm to 5 wppm diethyl acetal.

In one embodiment, the ethanol composition may comprise acetone, in an amount less than 500 wppm, e.g., less than 100 wppm, or less than 50 wppm. In terms of ranges, the ethanol composition may comprise from 10 wppm to 500 wppm acetone, e.g., from 30 wppm to 400 wppm acetone, or from 50 wppm to 300 wppm acetone. The inventive ethanol compositions may comprise acetaldehyde is in an amount of less than 18 wppm, e.g., less than 10 wppm, or less than 5 wppm.

Exemplary weight percentages for individual components are provided in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 85 to 99 | 90 to 96 | 92 to 96 |
| Water | <12 | <10 | <5 |
| Acetic Acid | <1 | <0.1 | <0.01 |
| Ethyl Acetate | <2 | <0.5 | <0.05 |
| Acetone | <0.05 | <0.01 | <0.005 |
| Isopropanol | 0.0095 to 0.085 | 0.01 to 0.08 | 0.011 to 0.04 |
| n-propanol | <0.5 | <0.1 | <0.05 |
| $C_4$ alcohols | <0.01 | <0.005 | <0.003 |
| $C_5$ alcohols | <0.003 | <0.0015 | <0.0005 |
| $C_6$ alcohols | <0.0010 | <0.0005 | <0.0001 |
| $C_{2+}$ alcohols | <0.75 | <0.5 | <0.1 |
| Acetaldehyde | <0.0018 | <0.0010 | <0.0005 |
| Diethyl acetal | <0.0010 | <0.0005 | <0.0002 |
| Methanol | <0.005 | <0.004 | 0 |
| Butanol | <0.002 | <0.0001 | 0 |
| 2-Butanol | <0.008 | <0.0008 | 0 |
| Isobutanol | <0.02 | <0.003 | 0 |
| Isoamyl alcohol | <0.02 | <0.0009 | 0 |
| Amyl alcohol | <0.02 | <0.0004 | 0 |

In other embodiments, the ethanol composition comprises very low amounts of metals, if any, e.g., the inventive ethanol composition comprises substantially no metals. For example, the inventive ethanol composition, in one embodiment, comprises less than 10 wppm copper, e.g., less than 1 wppm, less than 0.1 wppm, or less than 0.05 wppm. In one embodiment, the ethanol composition comprise substantially no copper, preferably the ethanol composition comprises no copper. In one embodiment, the inventive ethanol composition comprises substantially no heavy metals.

In one embodiment, the ethanol composition comprises very low amounts of inorganics. For example, the ethanol composition may comprise less than 20 mg/liter of chlorine/chloride, e.g., less than 10 mg/liter, less than 8 mg/liter or less than 5 mg/liter. In terms of parts per million, the ethanol composition may comprise less than 40 wppm chlorine/chloride, e.g., less than 20 wppm or less than 10 wppm. In one embodiment, the ethanol composition comprise substantially no chlorine, preferably the ethanol composition comprises no chlorine.

In one embodiment, the ethanol composition comprises less than 50 wppm sulfur, e.g., less than 30 wppm, less than 10 wppm, less than 7 wppm, less than 5 wppm, or less than 3 wppm. In one embodiment, the ethanol composition comprise substantially no sulfur, preferably the ethanol composition comprises no sulfur. In one embodiment, the ethanol composition may comprise less than 10 wppm of sulfate, e.g., less than 4 wppm, less than 3 wppm, less than 2 wppm, or less than 1 wppm. In one embodiment, the ethanol composition comprise substantially no sulfates, preferably the ethanol composition comprises no sulfates.

In one embodiment, the ethanol composition comprises less than 2 mg/liter of phosphorus, e.g., less than 1 mg/liter, less than 0.5 mg/liter, less than 0.3 mg/liter, less than 0.2 mg/liter, or less than 0.1 mg/liter. In one embodiment, the ethanol composition comprise substantially no phosphorus, preferably the ethanol composition comprises no phosphorus.

In one embodiment, the ethanol composition has a pHe ranging from 6.0 to 9.5, e.g., from 6.5 to 9.0. In one embodiment, the ethanol composition has a total acidity, as acetic acid, is less than 0.01 wppm, e.g., less than 0.007 wppm. In one embodiment, the ethanol composition has a total acidity, as acetic acid, is less than 65 mg/liter, e.g., less than 56 mg/liter or less than 30 mg/liter.

In another embodiment, the ethanol composition comprises at least one in situ denaturant, e.g., a denaturant that is co-produced with the ethanol. In these cases, the ethanol composition may be considered a "denatured ethanol composition." Preferably, the denatured ethanol composition comprises no denaturants that are not prepared in situ via the hydrogenation reaction. In one embodiment, the denatured ethanol composition comprises substantially no non-in situ denaturants. Because the denaturant is provided via the synthesis reaction, the denatured ethanol composition, as synthesized, beneficially requires no additional (outside) denaturants to form the denatured ethanol composition. As a result, the denatured ethanol composition, as synthesized, is suitable for commercial uses, e.g., is suitable for transportation as a denatured ethanol composition without further additions or processing. Exemplary weight percentage ranges for denatured ethanol compositions are shown in Table 8 (components other than ethanol and denaturants are also included in Table 8).

In some embodiments, the ethanol composition comprises an ethyl acetate denaturant in an amount ranging from 0.01 wt. % to 40 wt. % ethyl acetate, e.g., from 0.01 wt. % to 15 wt. %, from 0.01 wt. % to 10 wt. % or from 0.01 wt. % to 9 wt. %. In other embodiments, the ethanol composition comprises an acetaldehyde denaturant in an amount ranging from 0.01 wt. % to 10 wt. % acetaldehyde, e.g., from 0.01 wt. % to 5 wt. %, from 0.01 wt. % to 2 wt. % or from 0.01 wt. % to 1 wt. %. Preferably, the amount of total denaturant in these denatured ethanol compositions ranges from 0.01 wt. % to 20 wt. % denaturant, e.g., from 0.01 wt. % to 12 wt. % or from 0.01 wt. % to 10 wt. %.

TABLE 8

DENATURED ETHANOL COMPOSITIONS

| Component | Conc. (wt. %) | Conc. (wt. %) | Conc. (wt. %) |
|---|---|---|---|
| Ethanol | 50 to 99 | 60 to 99 | 70 to 95 |
| Water | 0.0001 to 1 | 0.001 to 0.1 | 0.001 to 0.05 |
| Acetic Acid | 1 to 20 | 3 to 15 | 5 to 10.5 |
| Ethyl Acetate (Denaturant) | <15 | <10 | <9 |
| Acetaldehyde (Denaturant) | <10 | <5 | <3 |
| Isopropanol (Denaturant) | 0.05 to 10 | 0.6 to 9 | 2 to 6.7 |
| Diethyl Ether (Denaturant) | 0.05 to 10 | 0.6 to 9 | 2 to 6.7 |
| N-propanol (Denaturant) | 0.05 to 10 | 0.6 to 9 | 2 to 6.7 |
| Acetal | <0.05 | <0.01 | <0.005 |
| Acetone | <0.05 | <0.01 | <0.005 |

In other embodiments, the invention is to specific compositions of ethanol and other organic components in specific component percentages. Examples of these specific compositions are shown below. For these compositions, the additional component and percentage features that are discussed elsewhere herein are also optionally applicable. For example, the ranges and/or limits for metal components and/or inorganics may be applicable to these compositions. Also, any of the component, percentage, or physical/chemical properties that are discussed herein are applicable to any of the contemplated ethanol compositions embodied herein.

An ethanol composition comprising:
(a) at least 85 wt. % ethanol;
(b) less than 12 wt. % water; and
(c) from 95 wppm to 850 wppm isopropanol.

An ethanol composition comprising:
(a) at least 85 wt. % ethanol;
(b) less than 8 wt % water;
(c) from 95 wppm to 850 wppm isopropanol; and
(d) methanol; and
(e) $C_{6+}$ alcohols.

In this embodiment, the amount of methanol and $C_{6+}$ alcohols, combined, is less than 50 wppm. Such a composition, e.g., as formed, has significantly less methanol and higher alcohols than an ethanol prepared via Fischer Tropsch synthesis. These additional alcohols are often difficult to separate from the ethanol and, as such, may remain in a Fischer Tropsch synthesized ethanol even after purification.

An ethanol composition comprising:
(a) at least 85 wt. % ethanol;
(b) from 95 wppm to 850 wppm isopropanol; and
(c) less than 10 wppm diethyl acetal.

An ethanol composition comprising:
(a) at least 85 wt % ethanol;
(b) from 95 wppm to 850 wppm isopropanol;
(c) methanol;
(d) $C_{6+}$ alcohols; and
(e) less than 10 wppm diethyl acetal.

In this embodiment, the amount of methanol and $C_{6+}$ alcohols, combined, is less than 50 wppm.

An ethanol composition comprising:
(a) at least 85 wt. % ethanol; and
(b) from 50 wppm to 500 wppm acetone.

An ethanol composition comprising:
(a) at least 85 wt % ethanol;
(b) from 50 wppm to 500 wppm acetone; and
(c) from 1 wppm to 850 wppm isopropanol.

An ethanol composition comprising:
(a) at least 85 wt. % ethanol;
(b) from 95 wppm to 850 wppm isopropanol; and
(c) from 10 wppm to 5000 wppm n-propanol.

An ethanol composition comprising:
(a) at least 85 wt. % ethanol;
(b) from 1 wppm to 850 wppm isopropanol;
(c) from 50 wppm to 500 wppm acetone;
(d) methanol; and
(e) $C_{6+}$ alcohols.

In this embodiment, the amount of methanol and $C_{6+}$ alcohols, combined, is less than 60 wppm.

An ethanol composition comprising:
(a) at least 85 wt. % ethanol;
(b) from 1 wppm to 850 wppm isopropanol; and
(c) less than 20 wppm butanol.

An ethanol composition comprising:
(a) at least 85 wt. % ethanol;
(b) from 95 wppm to 850 wppm isopropanol; and
(c) less than 30 wppm $C_4$-$C_5$ alcohols.

An ethanol composition comprising:
(a) at least 85 wt. % ethanol; and
(b) less than 10 wppm $C_{6+}$ alcohols.

An ethanol composition comprising:
(a) at least 85 wt. % ethanol;
(b) less than 10 wppm $C_{6+}$ alcohols; and
(c) less than 29 wppm acetaldehyde and $C_5$ alcohols, combined.

An ethanol composition comprising:
(a) at least 85 wt. % ethanol; and
(b) less than 9 wppm acetaldehyde and $C_5$ alcohols, combined.

An ethanol composition comprising:
(a) at least 85 wt. % ethanol;
(b) from 95 wppm to 850 wppm isopropanol; and
(c) at least 250 wppm alcohols other than isopropanol.

In this embodiment, the ethanol composition comprises an amount of alcohol impurities, a larger than average portion of which are isopropanol.

An ethanol composition comprising:
(a) from 50 wt. % to 99 wt. % ethanol;
(b) at least 1 wt. % of at least one denaturant selected from a group consisting of ethyl acetate, acetaldehyde, acetone, acetal, and n-propanol; and
(c) from 95 wppm to 850 wppm isopropanol.

The ethanol composition of claim 81, further comprising:
(d) methanol; and
(e) $C_{6+}$ alcohols;

In this embodiment, the amount of methanol and $C_{6+}$ alcohols, combined, is less than 60 wppm.

An ethanol composition comprising:
(a) from 50 wt. % to 99 wt. % ethanol;
(b) at least 1 wt. % of at least one denaturant selected from a group consisting of ethyl acetate, acetaldehyde, acetone, acetal, n-propanol; and
(c) isopropanol and acetone, wherein the ratio of isopropanol to acetone ranges from 1:15 to 1:0.1.

An ethanol composition produced directly from acetic acid made by the carbonylation reaction of methanol, the ethanol comprising:
(a) at least 85 wt. % ethanol;
(b) from 1 wppm to 850 wppm isopropanol; and
(c) less than 500 wppm n-propanol.

An ethanol composition synthesized via hydrogenation and purified using at least one distillation column, comprising:
(a) at least 85 wt. % ethanol;
(b) from 95 wppm to 850 wppm isopropanol; and
(c) less than 10 wppm diethyl acetal.

A synthesized ethanol composition comprising:
(a) at least 85 wt. % ethanol;
(b) from 1 wppm to 850 wppm isopropanol; and
(c) less than 16 wppm of butanol.

An ethanol composition synthesized via acetic acid hydrogenation comprising:
(a) ethanol; and
(b) from 0.1 wppm to 10 wppm diethyl acetal.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

In one embodiment, the inventive ethanol composition may be a component of a fuel composition. For example, the fuel composition may comprise a fuel component and the inventive ethanol, which may comprise isopropanol, e.g., in situ-formed isopropanol, in the amounts discussed herein. In some embodiments the fuel composition comprises non-in situ-formed alcohols, e.g., outside alcohols are added to the fuel composition. In one embodiment, the fuel composition comprises both in situ-formed isopropanol and non-in situ-formed isopropanol, e.g., outside isopropanol. Conventional ethanol compositions do not comprise in situ formed ispropanol in the amounts disclosed herein.

The finished ethanol composition may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid or reacted with polyvinyl acetate. The finished ethanol composition may be dehydrated to produce ethylene. Any of known dehydration catalysts can be employed in to dehydrate ethanol, such as those described in copending U.S. application Ser. No. 12/221,137 and U.S. application Ser. No. 12/221,138, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

In order that the invention disclosed herein may be more efficiently understood, a non-limiting example is provided below. The following examples describe various embodiments of the inventive ethanol composition.

EXAMPLES

Example 1

Several ethanol compositions were prepared using the hydrogenation process described above as well as the separation process. Crude ethanol products comprising ethanol, acetic acid, water and ethyl acetate were produced by reacting a vaporized feed comprising 95.2 wt. % acetic acid and 4.6 wt. % water with hydrogen in the presence of a catalyst comprising 1.6 wt. % platinum and 1 wt. % tin supported on ⅛ inch calcium silicate modified silica extrudates at an average temperature of 291° C., an outlet pressure of 2,063 kPa. Unreacted hydrogen was recycled back to the inlet of the reactor such that the total $H_2$/acetic acid molar ratio was 5.8 at a GHSV of 3,893 hr$^{-1}$. The crude ethanol products were purified using a separation scheme having distillation columns as shown in FIG. 1.

Table 9 shows compositional data for these ethanol compositions. The term "$C_{2+}$ alcohols" as used herein relates to alcohols having more than two carbon atoms.

TABLE 9

| FINISHED ETHANOL COMPOSITION RANGES | |
|---|---|
| Component | Avg. |
| Ethanol | 92.7 wt. % |
| Water | 7.4 wt. % |
| Acetic Acid | 14 wppm |
| Ethyl Acetate | 70 wppm |
| Isopropanol | 110 wppm |
| n-propanol | 160 wppm |
| $C_4$ alcohols | 21 wppm |
| $C_5$ alcohols | 0 |
| $C_{2+}$ alcohols | 291 wppm |
| Acetaldehyde | 5 wppm |
| Diethyl acetal | 1 wppm |
| Methanol | not detectable |

Comparative Example A

Table 10 shows data for a comparative ethanol composition prepared via fermentation of sugarcane.

TABLE 10

| COMPARATIVE ETHANOL COMPOSITION RANGES | |
|---|---|
| Component | Avg. |
| Ethanol | 93.4 wt. % |
| Water | 6.6 wt. % |
| Acetic Acid | 11 wppm |
| Ethyl Acetate | 51 wppm |
| Isopropanol | 2 wppm |
| n-propanol | 238 wppm |
| $C_4$ alcohols | 35 wppm |
| $C_5$ alcohols | 12 wppm |
| $C_{2+}$ alcohols | 288 wppm |
| Acetaldehyde | 29 wppm |
| Diethyl acetal | 59 wppm |
| Methanol | 51 wppm |

Comparative Example B

Table 11 shows data for a comparative ethanol composition prepared via fermentation of molasses.

TABLE 11

| COMPARATIVE ETHANOL COMPOSITION RANGES | |
|---|---|
| Component | Avg. |
| Ethanol | 93.4 wt. % |
| Water | 6.5 wt. % |
| Acetic Acid | 10 wppm |
| Ethyl Acetate | — |
| Isopropanol | 17 wppm |
| n-propanol | 109 wppm |
| $C_4$ alcohols | 20 wppm |
| $C_5$ alcohols | 11 wppm |
| $C_{2+}$ alcohols | 156 wppm |
| Acetaldehyde | 18 wppm |
| Diethyl acetal | 55 wppm |
| Methanol | 42 wppm |

Comparative Example C

Table 12 shows data for a comparative ethanol composition prepared via Fischer-Tropsch synthesis.

TABLE 12

COMPARATIVE ETHANOL COMPOSITION RANGES

| Component | Avg. |
| --- | --- |
| Ethanol | 93.1 wt. % |
| Water | 6.9 wt. % |
| Acetic Acid | 8 wppm |
| Ethyl Acetate | — |
| $C_4$ alcohols | 17 wppm |
| $C_5$ alcohols | 5 wppm |
| $C_{2+}$ alcohols | 261 wppm |
| Isopropanol | 10 wppm |
| n-propanol | 121 wppm |
| Higher alcohols | 131 wppm |
| Acetaldehyde | 4 wppm |
| Diethyl acetal | 10 wppm |
| Methanol | 46 wppm |

Surprisingly and unexpectedly, the amount of isopropanol in Example 1 is higher than in Comparative Examples A-C. Also, the amount of methanol in Example 1 is, advantageously, not detectable. In contrast, the amount of methanol in Comparative Examples A-C is significantly higher, e.g., 42 wppm to 51 wppm.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. An ethanol composition comprising:
(a) at least 85 wt. % ethanol;
(b) less than 12 wt. % water; and
(c) from 95 wppm to 850 wppm isopropanol; and
(d) n-propanol,
wherein the weight ratio of isopropanol to n-propanol is at least 0.5:1.

2. The ethanol composition of claim 1, wherein the ethanol composition comprises between 92 wt. % to 99 wt. % ethanol.

3. The ethanol composition of claim 1, wherein the ethanol composition between 7 wt. % to 8 wt. % water.

4. The ethanol composition of claim 1, further comprising less than 18 wppm acetaldehyde.

5. The ethanol composition of claim 1, further comprising less than 40 wppm methanol.

6. The ethanol composition of claim 1, wherein the ethanol composition comprises less than 0.5 wt % methanol.

7. The ethanol composition of claim 1, wherein the ethanol composition comprises no methanol.

8. The ethanol composition of claim 1, further comprising less than 10 wppm diethyl acetal.

9. The ethanol composition of claim 1, further comprising less than 5 wppm diethyl acetal.

10. The ethanol composition of claim 1, wherein the ethanol is not derived from fermentation.

11. The ethanol composition of claim 1, wherein the composition comprises less than 20 wppm chlorine.

12. The ethanol composition of claim 1, wherein the composition comprises no chlorine.

13. The ethanol composition of claim 1, wherein the composition comprises less than 40 wppm chlorine.

14. The ethanol composition of claim 1, wherein the composition comprises less than 1 wppm copper.

15. The ethanol composition of claim 1, wherein the composition comprises no copper.

16. The ethanol composition of claim 1, wherein the composition comprises less than 10 wppm copper.

17. The ethanol composition of claim 1, wherein the composition comprises less than 30 wppm sulfur.

18. The ethanol composition of claim 1, wherein the composition comprises no sulfur.

19. The ethanol composition of claim 1, wherein the composition comprises less than 50 wppm sulfur.

20. The ethanol composition of claim 1, wherein the composition comprises less than 4 wppm sulfates.

21. The ethanol composition of claim 1, wherein the composition comprises no sulfates.

22. The ethanol composition of claim 1, wherein the composition comprises less than 10 wppm sulfates.

23. The ethanol composition of claim 1, wherein the composition comprises less than 0.5 milligrams per liter phosphorus.

24. The ethanol composition of claim 1, wherein the composition comprises no phosphorus.

25. The ethanol composition of claim 1, wherein the composition comprises less than 2 milligrams per liter phosphorus.

26. The ethanol composition of claim 1, wherein the composition has a pHe ranging from 6 to 9.5.

27. The ethanol composition of claim 1, wherein the total acidity, as acetic acid, is less than 0.01 wppm.

28. The ethanol composition of claim 1, wherein the composition comprises from 0.5 wt. % to 1.5 wt. % branched alcohols.

29. The ethanol composition of claim 1, wherein the composition comprises less than 350 wppm alcohols other than ethanol.

30. An ethanol composition comprising:
(a) at least 85 wt. % ethanol;
(b) less than 8 wt % water;
(c) from 95 wppm to 850 wppm isopropanol; and
(d) methanol; and
(e) $C_{6+}$ alcohols;
wherein the amount of methanol and $C_{6+}$ alcohols, combined, is less than 50 wppm.

31. The composition of claim 30, further comprising from 0.1 wppm to 10 wppm diethyl acetal.

32. The composition of claim 30, wherein the composition comprises less than 10 wppm $C_{6+}$ alcohols.

33. An ethanol composition comprising:
(a) at least 85 wt. % ethanol;
(b) from 95 wppm to 850 wppm isopropanol; and
(c) diethyl acetal present in an amount less than 10 wppm.

34. The composition of claim 33, wherein the composition comprises 92 wt. % to 96 wt. % ethanol.

35. The composition of claim 33, further comprising more than 3 wt. % water.

36. The composition of claim 33, further comprising up to 12 wt. % water.

37. The composition of claim 33, further comprising up to 9 wt. % water.

38. The composition of claim 33, further comprising less than 40 wppm methanol.

39. The composition of claim 33, further comprising less than 18 wppm acetaldehyde.

40. The composition of claim 33, wherein the composition is derived from the hydrogenation of acetic acid.

41. The composition of claim 40, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

42. The composition of claim 33, further comprising $C_4$-$C_5$ alcohols in an amount less than 22 wppm.

43. The composition of claim 33, wherein the composition comprises less than 10 wppm $C_{6+}$ alcohols.

44. An ethanol composition comprising:
(a) at least 85 wt % ethanol;
(b) from 95 wppm to 850 wppm isopropanol;
(c) methanol;
(d) $C_{6+}$ alcohols; and
(e) less than 10 wppm diethyl acetal;
wherein the amount of methanol and $C_{6+}$ alcohols, combined, is less than 50 wppm.

45. An ethanol composition comprising:
(a) at least 85 wt. % ethanol; and
(b) from 50 wppm to 500 wppm acetone.

46. The composition of claim 45, wherein the composition comprises 92 wt. % to 99 wt. % ethanol.

47. The composition of claim 45, further comprising more than 3 wt. % water.

48. The composition of claim 45, further comprising up to 12 wt. % water.

49. The composition of claim 45, further comprising less than 10 wppm diethyl acetal.

50. The composition of claim 45, further comprising from 0.1 wppm to 10 wppm diethyl acetal.

51. The composition of claim 45, further comprising less than 18 wppm acetaldehyde.

52. The composition of claim 45, wherein the composition is derived from the hydrogenation of acetic acid.

53. An ethanol composition comprising:
(a) at least 85 wt % ethanol;
(b) from 50 wppm to 500 wppm acetone; and
(c) from 1 wppm to 850 wppm isopropanol.

54. The ethanol composition of claim 53, further comprising less than 10 wppm diethyl acetal.

55. The ethanol composition of claim 53, further comprising up to 12 wt. % water.

56. The ethanol composition of claim 53, further comprising less than 18 wppm acetaldehyde.

57. An ethanol composition comprising:
(a) at least 85 wt. % ethanol;
(b) from 95 wppm to 850 wppm isopropanol;
(c) from 10 wppm to 5000 wppm n-propanol; and
(d) from 0.1 wppm to 10 wppm diethyl acetal.

58. The composition of claim 57, further comprising from 50 wppm to 500 wppm acetone.

59. The composition of claim 57, wherein the composition comprises from 10 wppm to 100 wppm n-propanol.

60. An ethanol composition comprising:
(a) at least 85 wt. % ethanol;
(b) from 1 wppm to 850 wppm isopropanol;
(c) from 50 wppm to 500 wppm acetone;
(d) methanol; and
(e) $C_{6+}$ alcohols;
wherein the amount of methanol and $C_{6+}$ alcohols, combined, is less than 60 wppm.

61. The composition of claim 60, further comprising less than 10 wppm diethyl acetal.

62. The composition of claim 60, wherein the composition comprises from 95 wppm to 850 wppm isopropanol.

63. An ethanol composition comprising:
(a) at least 85 wt. % ethanol;
(b) from 1 wppm to 850 wppm isopropanol; and
(c) butanol present in an amount less than 20 wppm.

64. The composition of claim 63, further comprising less than 40 wppm methanol.

65. The composition of claim 63, further less than 10 wppm diethyl acetal.

66. An ethanol composition comprising:
(a) at least 85 wt. % ethanol;
(b) from 95 wppm to 850 wppm isopropanol; and
(c) $C_4$-$C_5$ alcohols present in an amount less than 30 wppm.

67. The composition of claim 66, further comprising less than 10 wppm diethyl acetal.

68. An ethanol composition comprising:
(a) at least 85 wt. ethanol;
(b) $C_{6+}$ alcohols present in an amount less than 10 wppm; and
(c) from 95 wppm to 850 wppm isopropanol.

69. The composition of claim 68, further comprising less than 40 wppm methanol.

70. The composition of claim 68, wherein the composition comprises less than 1 wppm $C_{6+}$ alcohols.

71. The composition of claim 68, further comprising less than 10 wppm diethyl acetal.

72. An ethanol composition comprising:
(a) at least 85 wt. % ethanol;
(b) less than 10 wppm $C_{6+}$ alcohols; and
(c) less than 29 wppm acetaldehyde and $C_5$ alcohols, combined, present in an amount less than 29 wppm.

73. The composition of claim 72, further comprising less than 10 wppm diethyl acetal.

74. An ethanol composition comprising:
(a) at least 85 wt. % ethanol;
(b) acetaldehyde and $C_5$ alcohols, combined, present in an amount less than 9 wppm; and
(c) isopropanol,
wherein the amount of acetaldehyde is less than the amount of isopropanol.

75. The composition of claim 74, further comprising less than 10 wppm diethyl acetal.

76. An ethanol composition comprising:
(a) at least 85 wt. % ethanol;
(b) from 95 wppm to 850 wppm isopropanol; and
(c) at least 250 wppm alcohols other than isopropanol.

77. The composition of claim 76, further comprising diethyl acetal in an amount less than 10 wppm.

78. An ethanol composition comprising:
(a) from 50 wt. % to 99 wt. % ethanol;
(b) at least 1 wt. % of at least one denaturant selected from a group consisting of ethyl acetate, acetaldehyde, acetone, acetal, and n-propanol;
(c) from 95 wppm to 850 wppm isopropanol; and
(d) acetaldehyde,
wherein the amount of acetaldehyde is less than the amount of isopropanol.

79. The ethanol composition of claim 78, wherein the denaturant is an in situ denaturant.

80. The ethanol composition of claim 78, wherein the acetal comprises diethyl acetal.

81. The ethanol composition of claim 78, further comprising:
(d) methanol; and
(e) $C_{6+}$ alcohols;
wherein the amount of methanol and $C_{6+}$ alcohols, combined, is less than 60 wppm.

82. An ethanol composition comprising:
(a) from 50 wt. % to 99 wt. % ethanol;
(b) at least 1 wt. % of at least one denaturant selected from a group consisting of ethyl acetate, acetaldehyde, acetone, acetal, n-propanol; and
(c) isopropanol and acetone, wherein the ratio of isopropanol to acetone ranges from 1:15 to 1:0.1.

83. An ethanol composition produced directly from acetic acid made by a carbonylation reaction of methanol, the ethanol composition comprising:
(a) at least 85 wt. % ethanol;
(b) from 1 wppm to 850 wppm isopropanol; and
(c) less than 500 wppm n-propanol
wherein the weight ratio of isopropanol to n-propanol is at least 0.5:1.

84. An ethanol composition synthesized via hydrogenation and purified using at least one distillation column, comprising:
(a) at least 85 wt. % ethanol;
(b) from 95 wppm to 850 wppm isopropanol; and
(c) diethyl acetal present in an amount less than 10 wppm.

85. An ethanol composition synthesized via acetic acid hydrogenation comprising:
(a) ethanol; and
(b) from 0.1 wppm to 10 wppm diethyl acetal.

86. The ethanol composition of claim 85, further comprising
(c) less than 29 wppm acetaldehyde and $C_5$ alcohols, combined.

87. The ethanol composition of claim 85, further comprising
(d) from 50 wppm to 500 wppm acetone.

88. The ethanol composition of claim 85, further comprising
(e) from 0.1 wppm to 10 wppm $C_{6+}$ alcohols.

89. An ethanol composition prepared by a process comprising the steps of:
hydrogenating an acetic acid feed stream in the presence of a catalyst to form a crude ethanol product;
separating at least a portion of the crude ethanol product in a first column into a first distillate comprising ethanol, water and ethyl acetate, and a first residue comprising acetic acid;
separating at least a portion of the first distillate in a second column into a second distillate comprising ethyl acetate and a second residue comprising ethanol and water; and
separating at least a portion of the second residue in a third column into a third distillate comprising the ethanol composition and a third residue comprising water;
wherein the ethanol composition comprises isopropanol and n-propanol and wherein the weight ratio of isopropanol to n-propanol is at least 0.5:1.

90. An ethanol composition prepared by a process for recovering the ethanol composition, comprising:
providing a crude ethanol product comprising ethanol, water, acetic acid, and ethyl acetate;
separating the crude ethanol product in a first column into a first distillate comprising ethanol, water and ethyl acetate, and a first residue comprising acetic acid;
separating the first distillate in a second column into a second distillate comprising ethyl acetate and a second residue comprising ethanol and water; and
separating the second residue in a third column into a third distillate comprising the ethanol composition and a third residue comprising water;
wherein the ethanol composition comprises isopropanol and n-propanol and wherein the weight ratio of isopropanol to n-propanol is at least 0.5:1.

\* \* \* \* \*